(12) United States Patent
Lemieux et al.

(10) Patent No.: US 6,358,686 B1
(45) Date of Patent: Mar. 19, 2002

(54) BRASSICA POLYMORPHISMS

(75) Inventors: Bertrand Lemieux, Sillery; Benoit S. Landry, Lacadie, both of (CA); Ronald J. Sapolsky, Mountain View, CA (US)

(73) Assignee: Affymetrix, Inc., Santa Clara, CA (US)

( * ) Notice: Subject to any disclaimer, the term of this patent is extended or adjusted under 35 U.S.C. 154(b) by 0 days.

(21) Appl. No.: 09/464,453

(22) Filed: Dec. 14, 1999

Related U.S. Application Data

(60) Provisional application No. 60/032,066, filed on Dec. 2, 1996.

(51) Int. Cl.$^7$ ................................................. C12Q 1/68
(52) U.S. Cl. ........................................ 435/6; 435/91.2
(58) Field of Search ..................... 435/6, 91.2; 53/23.1, 53/22.1, 24.33, 24.31

(56) References Cited

U.S. PATENT DOCUMENTS

| | | | |
|---|---|---|---|
| 5,206,137 A | 4/1993 | Ip et al. .......................... | 435/6 |
| 5,292,639 A | 3/1994 | Beitz et al. ..................... | 435/6 |
| 5,468,610 A | 11/1995 | Polymeropoulos et al. .... | 435/6 |
| 6,114,116 A | 9/2000 | Lemieux et al. ............... | 435/6 |

OTHER PUBLICATIONS

Ahouse et al., "Mouse MHC Class 1–Like FC Receptor Encoded Outside the MHC", *The Jrnl of Immunology*, vol. 151, No. 11, 1993, pp. 6076–6088.

Boardman et al., "Regulation of Expression of a Xenopus Borealia Embryonic/Larval α3 Skeletal–Actin Gene", *Eur. Jrnl. Biochem*, vol. 208, 1992, pp. 241–249.

Cross et al., "Purification of CPG Islands using a Methylated DNA Binding Column", *Nature Genetics*, vol. 6, 1994, pp. 236–244.

Fan et al., "Screening the Human Genome for Single–nucleotide Polymorphisms by Hybridization to High–density Oligonucleotide Arrays", *Mutation Detection*, May 29–Jun. 2, 1997, 1 page.

Gusella et al., "DNA Polymorphism and Human Disease", *Ann. Rev. Biochem*, vol. 55, 1986, pp. 831–854.

Hofte et al., "An Inventory of 1152 Expressed Sequence Tags Obtained by Partial Sequencing of cDNAs from Arabidopsis Thaliana", *The Plant Jrnl.*, vol. 4, No. 6, 1993, pp. 1051–1061.

Kwok et al., "Increasing the Information Content of STS–Based Genome Maps: Identifying Polymorphisms in Mapped STSs", *Genomics*, vol. 31, 1996, pp. 123–126.

Lok et al., "The Nucleotide Sequence of the 5'End of Papaya Mosaic Virus RNA: Site of In–Vitro Assembly Initiation", *Virology*, vol. 153, 1986, pp. 289–296.

Newman et al., "Genes Galore: A Summary of Methods for Accessing Results from Large–Scale Partial Sequencing of Anonymous Arabidopsis cDNA Clones", *Plant Physiol*, vol. 106, 1994, pp. 1241–1255.

Ohnuma et al., "Arachaebacterial Ether–Linked Lipid Biosynthetic Gene", *The Jrnl. Of Biological Chem.*, vol. 269, No. 20, 1994, pp. 14792–14797.

Purdy et al., Cloning, Nucleotide Sequence and Characterization of a Gene Encoding Superoxide Dismutase from Campylobacter Jejuni and Campylobacter Coli, *Microbiology*, vol. 140, 1994, pp. 1203–1208.

Saiki et al., "Analysis of Enzymatically Amplified β–Globin and HLA–DQ α DNA With Allele–Specific Oligonucleotide Probes", *Nature*, vol. 324, No. 13, 1986, pp. 163–166.

Wilson et al., "2.2MB of Contiguous Nucleotide Sequence from Chromosome III of C. Elegans", *Nature*, vol. 368, 1994, pp. 32–38.

Wharton et al., "Nucleotide Sequence from the Neurogenic Locus Notch Implies a Gene Product that Shares Homology with Proteins Containing EGF–Like Repeats", *Coil*, vol. 43, 1985, pp. 567–581.

*Primary Examiner*—Eggerton A. Campbell
(74) *Attorney, Agent, or Firm*—Townsend and Townsend and Crew LLP

(57) ABSTRACT

The invention provides oligonucleotides and their complements that can be used as allele-specific probes or primers for sequencing, oligonucleotide probe hybridization, and allele-specific amplification. Such oligonucleotides can be used, for example, to facilitate genetic distinction between individual plants in plant populations.

15 Claims, 1 Drawing Sheet

US 6,358,686 B1

BRASSICA POLYMORPHISMS

CROSS-REFERENCE TO RELATED APPLICATION

The present application derives priority from provisional application 60/032,069, filed Dec. 2, 1996, which is incorporated by reference in its entirety for all purposes.

COPYRIGHT NOTICE

This disclosure contains material which is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

BACKGROUND OF THE INVENTION

The genomes of all organisms undergo spontaneous mutation in the course of their continuing evolution generating variant forms of progenitor sequences (Gusella, *Ann. Rev. Biochem.* 55, 831–854 (1986)). The variant form may confer an evolutionary advantage or disadvantage relative to a progenitor form or may be neutral. In some instances, a variant form confers a lethal disadvantage and is not transmitted to subsequent generations of the organism. In other instances, a variant form confers an evolutionary advantage to the species and is eventually incorporated into the DNA of many or most members of the species and effectively becomes the progenitor form. In many instances, both progenitor and variant form(s) survive and co-exist in a species population. The coexistence of multiple forms of a sequence gives rise to polymorphisms.

Several different types of polymorphism have been reported. A restriction fragment length polymorphism (RFLP) means a variation in DNA sequence that alters the length of a restriction fragment as described in Botstein et al., *Am. J. Hum. Genet.* 32, 314–331 (1980). The restriction fragment length polymorphism may create or delete a restriction site, thus changing the length of the restriction fragment. RFLPs have been widely used in human and animal genetic analyses (see WO 90/13668; WO90/11369; Donis-Keller, Cell 51, 319–337 (1987); Lander et al., *Genetics* 121, 85–99 (1989)). When a heritable trait can be linked to a particular RFLP, the presence of the RFLP in an individual can be used to predict the likelihood that the animal will also exhibit the trait.

Other polymorphisms take the form of short tandem repeats (STRs) that include tandem di-, tri- and tetra-nucleotide repeated motifs. These tandem repeats are also referred to as variable number tandem repeat (VNTR) polymorphisms. VNTRs have been used in identity and paternity analysis (U.S. Pat. No. 5,075,217; Armour et al., *FEBS Lett.* 307, 113–115 (1992); Horn et al., WO 91/14003; Jeffreys, EP 370,719), and in a large number of genetic mapping studies.

Other polymorphisms take the form of single nucleotide variations between individuals of the same species. Such polymorphisms are far more frequent than RFLPs, STRs and VNTRs. Some single nucleotide polymorphisms occur in protein-coding sequences, in which case, one of the polymorphic forms may give rise to the expression of a defective or other variant protein. Other single nucleotide polymorphisms occur in noncoding regions. Some of these polymorphisms may also result in defective or variant protein expression (e.g., as a result of defective splicing). Other single nucleotide polymorphisms have no phenotypic effects. Single nucleotide polymorphisms can be used in the same manner as RFLPs, and VNTRs but offer several advantages. Single nucleotide polymorphisms occur with greater frequency and are spaced more uniformly throughout the genome than other forms of polymorphism. The greater frequency and uniformity of single nucleotide polymorphisms means that there is a greater probability that such a polymorphism will be found in close proximity to a genetic locus of interest than would be the case for other polymorphisms. Also, the different forms of characterized single nucleotide polymorphisms are often easier to distinguish that other types of polymorphism (e.g., by use of assays employing allele-specific hybridization probes or primers).

Despite the increased amount of nucleotide sequence data being generated in recent years, only a minute proportion of the total repository of polymorphisms has so far been identified. The paucity of polymorphisms hitherto identified is due to the large amount of work required for their detection by conventional methods. For example, a conventional approach to identifying polymorphisms might be to sequence the same stretch of oligonucleotides in a population of individuals by didoxy sequencing. In this type of approach, the amount of work increases in proportion to both the length of sequence and the number of individuals in a population and becomes impractical for large stretches of DNA or large numbers of subjects.

SUMMARY OF THE INVENTION

The invention provides nucleic acid segments containing at least 10, 15 or 20 contiguous bases from a fragment shown in Table 1 including a polymorphic site. Complements of these segments are also included. The segments can be DNA or RNA, and can be double- or single-stranded. Some segments are 10–20 or 10–50 bases long. Preferred segments include a diallelic polymorphic site.

The invention further provides allele-specific oligonucleotides that hybridizes to a segment of a fragment shown in Table 1 or its complement. These oligonucleotides can be probes or primers. Also provided are isolated nucleic acids comprising a sequence of Table 1 or the complement thereto, in which the polymorphic site within the sequence is occupied by a base other than the reference base shown in Table 1.

The invention further provides a method of analyzing a nucleic acid from a subject. The method determines which base or bases is/are present at any one of the polymorphic sites shown in Table 1. Optionally, a set of bases occupying a set of the polymorphic sites shown in Table 1 is determined. This type of analysis can be performed on a plurality of subjects who are tested for the presence of a phenotype. The presence or absence of phenotype can then be correlated with a base or set of bases present at the polymorphic sites in the subjects tested.

DEFINITIONS

Figure 1:
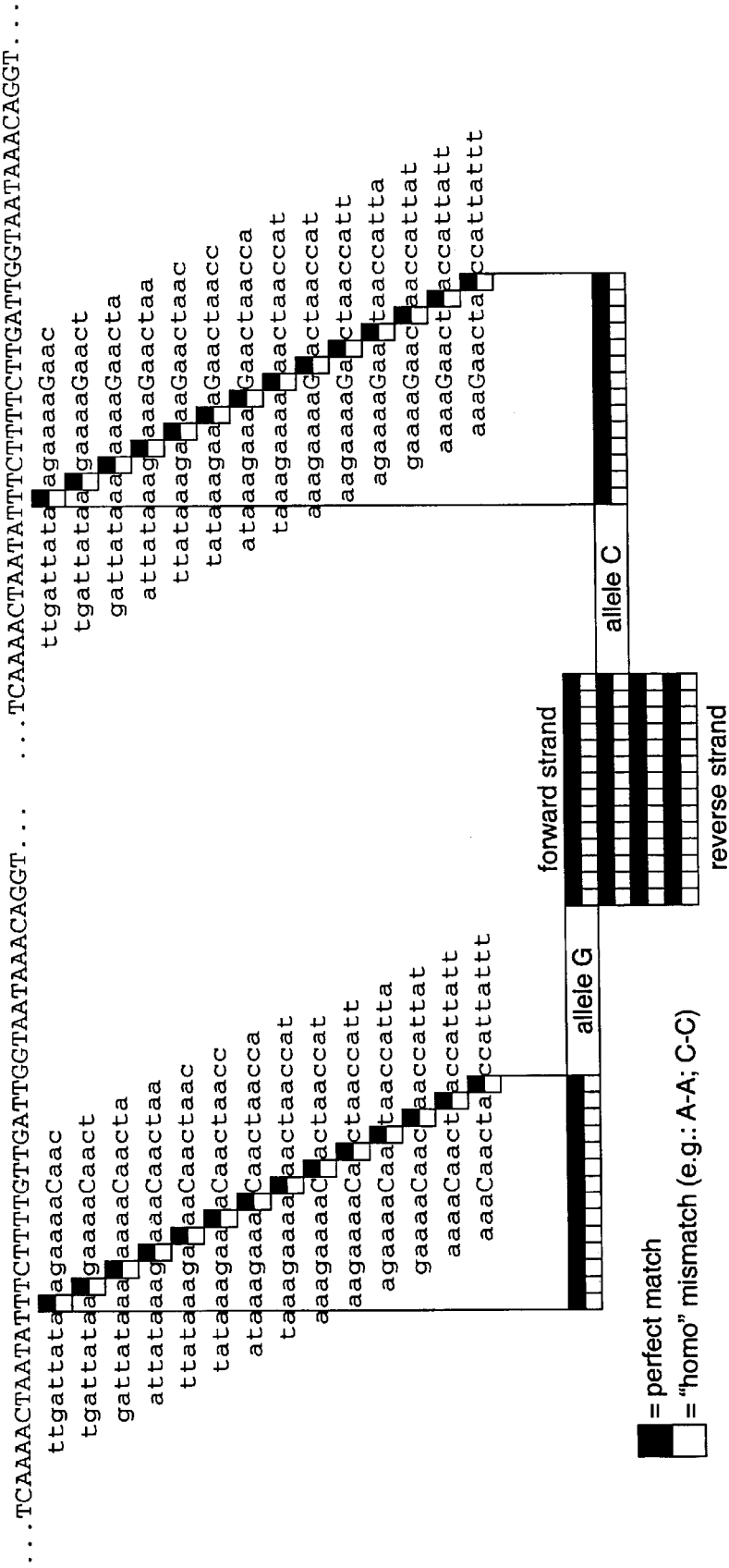
FIG. 1 shows probe array tiles (SEQ ID NOS:3–29) for two allelic forms of the Brassica 18A2 polymorphism (SEQ ID NOS:1 and 2).

A nucleic acid, such an oligonucleotide, oligonucleotide can be DNA or RNA, and single- or double-stranded. Oligonucleotides can be naturally occurring or synthetic, but are typically prepared by synthetic means. Preferred nucleic acids of the invention include segments of DNA, or their complements including any one of the polymorphic sites shown in Table 1. The segments are usually between 5 and 100 bases, and often between 5–10, 5–20, 10–20, 10–50, 20–50 or 20–100 bases. The polymorphic site can occur within any position of the segment. The segments can be from any of the allelic forms of DNA shown in Table 1. Methods of synthesizing oligonucleotides are found in, for example, *Oligonucleotide Synthesis: A Practical Approach* (Gait, ed., IRL Press, Oxford, 1984).

Hybridization probes are oligonucleotides capable of binding in a base-specific manner to a complementary strand of nucleic acid. Such probes include peptide nucleic acids, as described in Nielsen et al., *Science* 254, 1497–1500 (1991).

The term primer refers to a single-stranded oligonucleotide capable of acting as a point of initiation of template-directed DNA synthesis under appropriate conditions (i.e., in the presence of four different nucleoside triphosphates and an agent for polymerization, such as, DNA or RNA polymerase or reverse transcriptase) in an appropriate buffer and at a suitable temperature. The appropriate length of a primer depends on the intended use of the primer but typically ranges from 15 to 30 nucleotides. Short primer molecules generally require cooler temperatures to form sufficiently stable hybrid complexes with the template. A primer need not reflect the exact sequence of the template but must be sufficiently complementary to hybridize with a template. The term primer site refers to the area of the target DNA to which a primer hybridizes. The term primer pair means a set of primers including a 5' upstream primer that hybridizes with. the 5' end of the DNA sequence to be amplified and a 3', downstream primer that hybridizes with the complement of the 3' end of the sequence to be amplified.

Linkage describes the tendency of genes, alleles, loci or genetic markers to be inherited together as a result of their location on the same chromosome, and can be measured by percent recombination between the two genes, alleles, loci or genetic markers.

Polymorphism refers to the occurrence of two or more genetically determined alternative sequences or alleles in a population. A polymorphic marker or site is the locus at which divergence occurs. Preferred markers have at least two alleles, each occurring at frequency of greater than 1%, and more preferably greater than 10% or 20% of a selected population. A polymorphic locus may be as small as one base pair. Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified allelic form is arbitrarily designated as a the reference form and other allelic forms are designated as alternative or variant alleles. The allelic form occurring most frequently in a selected population is sometimes referred to as the wildtype form. Diploid organisms may be homozygous or heterozygous for allelic forms. A diallelic polymorphism has two forms. A triallelic polymorphism has three forms.

A single nucleotide polymorphism occurs at a polymorphic site occupied by a single nucleotide, which is the site of variation between allelic sequences. The site is usually preceded by and followed by highly conserved sequences of the allele (e.g., sequences that vary in less than 1/100 or 1/1000 members of the populations).

A single nucleotide polymorphism usually arises due to substitution of one nucleotide for another at the polymorphic site. A transition is the replacement of one purine by another purine or one pyrimidine by another pyrimidine. A transversion is the replacement of a purine by a pyrimidine or vice versa. Single nucleotide polymorphisms can also arise from a deletion of a nucleotide or an insertion of a nucleotide relative to a reference allele.

Hybridizations are usually performed under stringent conditions, for example, at a salt concentration of no more than 1 M and a temperature of at least 25° C. For example, conditions of 5×SSPE (750 mM NaCl, 50 mM NaPhosphate, 5 mM EDTA, pH 7.4) and a temperature of 25–30° C. are suitable for allele-specific probe hybridizations.

Nucleic acids of the invention are often in isolated form. An isolated nucleic acid means an object species that is the predominant species present (i.e., on a molar basis it is more abundant than any other individual species in the composition). Preferably, an isolated nucleic acid comprises at least about 50, 80 or 90 percent (on a molar basis) of all macromolecular species present. Most preferably, the object species is purified to essential homogeneity (contaminant species cannot be detected in the composition by conventional detection methods).

DESCRIPTION OF THE PRESENT INVENTION

I. Novel Polymorphisms of the Invention

The present application provides oligonucleotides containing polymorphic sequences isolated from two Brassica species, *B. napus* and *B. oleracea*. The invention also includes various methods for using those novel oligonucleotides to identify, distinguish, and determine the relatedness of individual strains or pools of nucleic acids from plants within the family Cruciferae.

The genus Brassica is part of the family Cruciferae. Members of the Brassica genus have been described as Old World Temperate Zone herbs of the mustard family with beaked cylindrical pods. Merriam-Webster=s Collegiate Dictionary, Tenth ed., p.139 (1993). Many cruciferous plants are important agricultural items and include many foodstuffs (condiments, oilseeds, and vegetables). For example, canola (a type of *Brassica napus*) is one of the largest crops in Canada.

The sequences in Table 1 were isolated from *B. napus* and *B. oleracea* using oligonucleotide primers designed from expressed DNA sequences from *Arabidopsis thaliana*, a relative of *Brassica napus* and member of the Cruciferae family. See Hofte et al., An inventory of expressed sequence tags obtained by partial sequencing of cDNAs from *Arabidopsis thaliana*, 169 *Plant J.*, Vol. 4, pp. 1051–1061 (1993) and Newman et al., Genes Galore: A Summary of Methods for Accessing Results from Large-Scale Partial Sequencing of Anonymous Arabidopsis cDNA Clones, *Plant Physiol.*, Vol. 106, pp. 1241–1255 (1994). There is a high degree of homology between the coding sequences of Arabidopsis, Brassica, and other members of the Cruciferae family.

The designations in Table 1 are as follows. The first number, preceding the "–" is an arbitrarily assigned identification number for a polymorphism. The first number after the "–" is the Brassica strain name corresponding to the upper allele sequence. The next number designates the primer pair used for the PCR amplification. The sequences of primers are described at the web site (http://www.yorku.ca/ftp/york_other/cgat/) (incorporated by reference in its entirety for all purposes). The last number is the name of the strain for the lower allele sequence. For example 1-85/5B5/86-1 means that polymorphic site 1 was identified by comparing strains 85 and 86-1 at a segment amplified by primers 5B5. Each sequence in the table includes a polymorphic site shown in square brackets [] and flanking bases common to both strains being compared. The upper and lower sequences in the square brackets are from the two strains being compared (upper strand corresponding to the first designated strain). A "/" within square brackets followed or preceded by a blank space represents an addition/deletion polymorphism. Sequences having marker names with a single/(such as 24-10C8/N2), indicate a polymorphic position but do not show comparisons with a second strand. An asterisk indicates triallelic markers. The designation N in Table 1 indicates a base whose identity was not determined.

| Marker Name | Sequence | SEQ ID NO |
|---|---|---|
| 1-85/5B5/86-1 | AGCAAGCTTACATGCGTGGA[GT/AA]GAGAGTCCTCGAGATCAACC | 30 |
| 2-85/5B12/N3-1 | CCTTGATCTCTCAAGTAATC[A/G]TCTCACCGGAAGATCCCTGA | 31 |
| 3-85/5C3/86-2 | ACCATCCATTAAACTGTATC[A/G]TCGCAATCTAACCAAAAGTT | 32 |
| 4-85/5E1/86-1 | TAAAGCAAAGAGAGTCTTAC[C/A]GTCTGCTGCATGATATACCC | 33 |
| 5-85/5E1/86-2 | CTACTGATAGTGAACCACCC[A/C]ATCCCCAAATTTAAAGCAAA | 34 |
| 6-85/6A11/86 | ATCCTATTGGTAGTAACACA[G/A]ATTGAGTTAATGTTGCAGGG | 35 |
| 7-N1/6A11/N2 | AGGCAAAGCGGTAGTTGCAA[G/A]ACTGCTTCTCACGAGGTAAT | 36 |
| 8-N1/6A9/N2-1 | CCAGCTTCAATGTCTGCATG[C/A]TTGTGTCGATGCCAAAGTTC | 37 |
| 9-N1/6A9/N2-2 | AAAGTTCATTACGATGATCT[A/G]ACCCTGCAGTCATCCATGGA | 38 |
| 10-85/6A12/86 | CTTCCCCCCCTCAATACCTC[T/G]TTCAAAAGTGAAAAGTGCAG | 39 |
| 11-N1/6D1/N2-1 | ATTTTGTTTTGTTTCTTGTC[G/C]GGTCAGGTCAGAACAAAGTT | 40 |
| 12-N1/6H5/N2 | AAACCAGAGCCACCTCCTTA[C/]CCACCTCATCGTTTCCTTTC | 41 |
| 13-86/6F11/N2-2 | GATTTCGACCGCAGTCTCAC[G/T]GAGGATGAGTATATCGCTTT | 42 |
| 14-N1/6F11/N2 | TAGGACAGGCAAACAATTCTA[C/A]GCGGTCAAAATCCGATTTCG | 43 |
| 16-N1/8B5/N2 | ACTCAAAAAAACGATACCTC[G/C]GCCGTCTCTCGCCGTCTCGC | 44 |
| 17-N1/8D4/N2-1 | CAGGAGACAGTTACAGTCCC[/A]CAGAGTCGCAAGGATCTCGAA | 45 |
| 18-85/8D4/86-2 | CTGATCTTGAAGGAGAGACC[A/G]CCACAAGGTTCCATCCTATG | 46 |
| 19-85/8H11/86 | AGTGCgAGGCTCAGTTGGAT[G/T]ATTAGGGTGTCAGTAAATCA | 47 |
| 20-85/10B8/86 | NAGGTCCATGATGATGACAA[T/A]AAAGGTATTCCACATGTCAA | 48 |
| 21-N2/10B8/N3-2 | ACATCCAACTTTTCTCCAGT[T/C]CTTTATTCTATCCTGATTTG | 49 |
| 21-N2/10B8/N3-2 | ACATCCAACTTTTCTCCAGT[T/C]CTTTATTCTATCCTGATTTG | 50 |
| 22-N2/10B8/N3-1 | AAGGTATTCCATTGGTATAC[A/C]TCCAACTTTTCTCCAGTTCT | 51 |
| 23-85/10B9/86 | GACCTTCTTGGGAAAGAAAG[T/C]TGTAACCGCGTCGAGATTCG | 52 |
| 24-10C8/N2 | ATAGAAACCGCCGATGCTCA[A]GGACACGCCACCGTCTTCGT | 53 |
| 25-10C8/N2 | CACTTTCTTCGTGGCTAAAT[T]CTTCGGCCGAGCCGGTCTCA | 54 |
| 26-10D2/N1 | GTTATCATCAGTACCGGTAT[T]AACCCCAAGGCTAATTCTTA | 55 |
| 27-85/10D2 | TTGGGTATCTACGGACTGAT[C]ATCGCTGTTATCATCAGTAC | 56 |
| 28-N1/10E12/N2-1 | GGAATTCAATACTCGCCAAC[G/T]TCTTCATTGCTGTCGTCGGC | 57 |
| 29-N1/10E12/N2-2 | TCCTTACGCCTTCAAGCGCA[C/G]CGGCTGGCTCATGGGTGTCC | 58 |
| 30-N1/10F4/N2 | TGTATCTATGCGGTGGCTGC[G/C]GTCTCCGTTCGCGCCAGTAC | 59 |
| 31-10F4/N2 | GCGCCAGTACCGCCGGTTAC[A]ATCTcACTGCCTTCACGTCC | 60 |
| 32-85/10F4/N2 | GCGCCAGTACCGCCGGTTAC[G/A]ATCTTAATGCCTTCACGTTC | 61 |
| 33-85/10F9/N1-2 | AACTTGGAATTCCACAACTT[G/C]AGAAACTTCGATGTGGTGCC | 62 |
| 34-85/10F9/86 | CGGTACTGCGAAAGCTGGAG[C/G]ATCAACTTGGAATTCCACAA | 63 |
| 35-86/10F12 | AAAAGTGCTATTGTTCAGGT[G]GATGCTGCTCCGTTCAAGCA | 64 |
| 36-85/10H6/86 | GTCAAAAGCCACGGATTCAA[G/A]AACGTGCTCTTCTTGCGCCT | 65 |
| 38-85/10F12/86 | AAACCAGGGTCCTTGATGTG[T/]GTCTACAACGCTTCCAACAA | 66 |
| 39-85/11B7/86 | AANACCCTGAGCTCATGCCT[C/T]TGACCCATGTTCTTGCCACC | 67 |
| 40-85/11C4/86 | TTTGGGACCGTTGGAGTTGC[A/G]TCTGCGGCTATGACGGTGGA | 68 |
| 41-85/11D4/86-2 | AATCTTTGCCATTGCTGTCA[A/G]TATCTTCGTCAGCTTCAGCT | 69 |
| 43-N2/11D11/N3 | GACAACGCTGGTGGTATTGC[C/T]GAAATGGCTGGAATGAGCCA | 70 |
| 44-86/11D11/N3 | GCTGCTCTAGGGATGCTCAG[C/T]ACCATCGCCACCGGTTTGGC | 71 |
| 45-85/11D11/86 | ATGCTCAGCACCATCGCCAC[TC]GGTTTgGCGATTGATGCTTA | 72 |
| 46-N2/11E3/N8a | GAGAAAGTGCTTGTGGAGAT[C/T]TACAaGTCCATACTGATGGC | 73 |
| 47-86/11E3/N2a | AATGCTTGTGGAGATtTACA[G/A]GTCCATACTGATGGCGCAGG | 74 |
| 48-86/11E3/N2b | AATGCTTGTGGAGATcTACA[G/A]GTCCATACTGATGGCGCAGG | 75 |
| 49-85/11F12/86 | AATGATTGGTTTGAGAAGCA[T/A]ACAGCTGGTACGCTTGATAT | 76 |
| 50-85/11F7/86 | GATAGGGCGAAGAGAGGGAA[G/A]AGTCCTGAGAGGAAAGAGAT | 77 |
| 51-85/11H2/86-2 | CTCTCTCTCCACAAAGACAC[A/C]GCTTTCTCCATGACCTTCGG | 78 |
| 52-85/11H5/86-2 | TCTCTGACGTCATGAAAGCT[C/A]ATGGCAAAATTGGTGATGGA | 79 |
| 53-85/11H6/86-1a | GTTATCGATCGCGTGGTCCG[T/C]GAAACCCAAAATaCACCTTT | 80 |
| 54-85/11H6/86-1b | GTTATCGATCGCGTGGTCCG[T/C]GAAACCCAAAATtCACCTTT | 81 |
| 55-85/12B6/N3 | CGTCAGCCTTCTTCCGCCGC[A/C]GTCGTCCTCCGCAACCGTGC | 82 |
| 56-86/12B6/85a | TGTCTCTTCCGTCAGCCTTC[C/T]TCCGCCGCAGTCGTCCTCCG | 83 |
| 57-86/12B6/85b | TGTCTCTTCCGTCAGCCTTC[C/T]TCCGCCGCCGTCGTCCTCCG | 84 |
| 58-86/12B11/85 | TCAGGTTTACCTCTATATAT[T/]ATATTTCATGGTATGAAGGT | 85 |
| 59-n1/12B11/N2-2 | TATCCTGCAAATTGACATTT[T/C]CCTTCAGGTTCTAGAAGCTG | 86 |
| 60-85/12C2/86 | CGAGAACAGAAGAGAAGAGA[C/]TGGAACACGTCGGACAGTAC | 87 |
| 62-12C11/N2 | ACGGGTCCTAGCGCCATGGC[T]ATTTTCCTCACCGTTTCTGG | 88 |
| 63-N1/12D10 | TTGGGCTTTCGGTGGTATGA[T]CTTCGTCCTCGTCTATTGCA | 89 |
| 65-85/12F4/86-1 | TCCTTGATTCCTTAATAATC[A/T]TTGGCTGGGGGTCTTTCTAA | 90 |
| 66-12G5/N1 | GCTTGAATAACGATGTCTAC[T]CTGCCTCGGCGTACGGCGGA | 91 |
| 67-85/12G8 | CTAAAAAGATCGACGAGTGT[C]CCTTACTACGCTCCATCTAT | 92 |
| 68-12G9/N1-1 | AGGTGGGTTTAGCGTGGCAT[C]CGATCCATTGGATGGATCCA | 93 |
| 69-85/12G9/ | NGTGGGTTTACCGTATCATT[T]GATCCATTGGATGGATCGAG | 94 |
| 70-12B11/N2-1 | GCGGATCCTATATTGGGTCT[T]GATGGATTGTTTCTATCCCG | 95 |
| 71-/12B11/N2-2 | TATCCTGCAAATTGACATTT[C]CCTTCAGGTTCTAGAAGCTG | 96 |
| 72-N1/12E10 | TACCACGGTCGTACTGGTCG[A]TGTCTGGAACGTCACCAAGC | 97 |

-continued

| Marker Name | Sequence | SEQ ID NO |
|---|---|---|
| 73-N1/13A3/N2a | CTGTCTCAgTTTGTTGGATC[C/G]AAATCgAATCGAAAGCGTAC | 98 |
| 74-N1/13A3/N2b | CTGTCTCAgTTTGTTGGATC[C/G]AAATCaAATCGAAAGCGTAC | 99 |
| 75-13E8/N2 | ACACTGTTGGAGGACGTGAA[G]AAGATATTCAAGACAACATC | 100 |
| 76-N1/13F6/N2-2 | TCTTTCGTATCTTGCTGAGT[C/T]GTTACGCCTGTCAACACCCG | 101 |
| 77-13F8/N2-1 | GGAACCCTAGGGAGCCCACA[G]CTCCTTATGCTAAGCGGCGT | 102 |
| 78-13F8/N2 | GATCATAGTATCCGCCGGAA[C]CCTAGGGAGCCCACAGCTCC | 103 |
| 79-85/14B5/86 | TTCGGCGGGTCGATCCGGGC[A/G]GAAGACATTGTCAGGTGANN | 104 |
| 80-N1/14C2/N2 | GCACCAACATTGTAAACCTA[T/G]AGCTTCTTCCTCAGCCACCT | 105 |
| 81-85/14C2/86-1 | GCTGCCACATAGTGAACCTA[T/A]AGCTTCTTCCTCAGCCACCT | 106 |
| 82-N2/14C2/85-2 | GCACCAACATTGTGAACCTA[G/A]AGCTTCTTCCTCAGCCACCT | 107 |
| 83-85/14C2/86-2 | AGTACATAGCTATTGACTAA[C/G]TTAAGTTCCTTGTATTGTTG | 108 |
| 84-N2/14C2/85-1 | CCTCTATCCGCCATGGTTGC[A/T]CCAACATTGTGAACCTAGAG | 109 |
| 85-85/14E2/86-2 | TTGACCCTCGGCAAGCCACC[G/T]GTCAAGCCATGCTGCAGCCT | 110 |
| 86-85/14E2/86-1 | AGGCTGCCCTCTCCCAATTC[A/C]AAAGCCAACTCCTAAACCAA | 111 |
| 87-85/14E8/86 | AAACATGGAAAGGCCTGATA[/G]TCACCGTCAAGCTCACCGTC | 112 |
| 88-85/14E12/86 | CAACCTGAAAAATTGTTTTA[C/A]CAACGGCCCCGCTTTCTCCA | 113 |
| 89-14H10/86 | AAGGCCAACAACGACATTAC[C]TCCATCGTTAGCAACGGAGG | 114 |
| 90-85/14H10/86 | TCACCGGCTTGAAGTCTTCC[G/T]CTGCATTCCCAGTCACCCGC | 115 |
| 91-85/15A6/86 | ACTCAGCTTTCTTATGCCTC[G/]ACTTGCGACACACGAATCCA | 116 |
| 92-85/15C4/86 | TGCGGCTAACATCTCTGGTG[G/T]TCACCTTAACCCAGCCGTAN | 117 |
| 93-85/15E5/86-1 | CGAGGATCACTTCTCTCTGT[G/T]CAAGAAGAAGTTCGGcAAGG | 118 |
| 94-N1/15E5/N2-1 | CTGTtCAAGAAGAAGTTCGG[C/T]AAGGTCTACGCTTCCCGCGA | 119 |
| 95-N1/15E5/N2-2 | CCCTCTGCTCGTCACGGCGT[T/A]ACGCAGTTCTCGGATCTGAC | 120 |
| 96-86/15E5/N2 | CCCGCGAGGAGCACGACTAC[A/T]GATTCTCCGTTTTCAAATCC | 121 |
| 97-15E9/86 | TCCACTCGCCGGGAAGAAAC[T]CGACAAACCGTTGTCTACTT | 122 |
| 98-N2/15E9 | ATGGCTCGCGACGGGTCTCC[G]GTAAACTCGGAGAGCAGAT | 123 |
| 99-N2/15E9/86 | GCCGACTCTCGAAGCTTCTT[A/]ACTCCACTCGCCGGGAAGAA | 124 |
| 100-85/15E9/86-1 | GAATCTAGGAGAGCAGATCT[T/G]CCTCTCTATCTTCAATGTTC | 125 |
| 101-85/15E9/86-2 | TCCACTCGCCGGGAAGAAAC[C/T]CGACAAACCGTTGTCTACAT | 126 |
| 102-N1/15E9/N2-1 | GTCATGAAGATATTCACTAC[A/G]CCGACTCTCGAAGCTTCTTA | 127 |
| 103-85/15F1/86 | GCAGGTAAAATTCTACAGAC[C/A]TTCCCTTTTCATTGTAGTTA | 128 |
| 105-85/15F10/86 | GTGCCCTAAAGATACCCTCA[A/G]GCTTGGTGTCTGCGCTAATG | 129 |
| 106-N2/15G1 | TTCTTCCCACAGGTGAAACT[T]GCTAACTTCCTTCCAAAGTA | 130 |
| 107-N1/15H7/N2 | TATGTATCAGGACAATGTGT[GA/TT]GTGACTGTGGTTGCATCCAT | 131 |
| 108-N1/16A1/N2-1 | GCTAAGCTACGCAACTGCCA[C/T]CAATCAGGGCAAGCTAAAGG | 132 |
| 109-85/16A5/86 | TATACACTCTTTAAAAGCGT[G/C]TGTGTGTACCCATCTCTCTT | 133 |
| 110-N1/16B6/N2 | ATGGCTGCGTATTGGCTGTC[C/T]AAGGCTGGATCTTGGTCCCA | 134 |
| 111-85/16B6/N1 | GGATCCATCTCAACTATGGT[A/C]GTATTACGTTGAGGCTAGG | 135 |
| 112-85/16B7/86 | GTATGTGATTCGGAAGAGAA[T/]CAAACTAAGTGCCGAGAAAG | 136 |
| 113-N1/16D6/N2 | GCTAAGGTAGTTGGAGGAGC[CAA/GTG]CCACAGCCACGCGACTAAGG | 137 |
| 114-85/16D10/86 | CTCAACGTAGCAAGTAATAA[T/G]ATACTGTCTATTTATGGTTA | 138 |
| 115-N1/16E9/N2 | AGACTTTCCCCATTCTCTTC[T/A]CCATCCACCGTCGAAACCCA | 139 |
| 116-85/16H3/86-1 | ACTTCGAAACTGTAAACCTA[A/T]ACTTTAAGAGTTTAGAGCTA | 140 |
| 117-85/16H3/86-2 | CACCATCGGAGAAAGAGGTA[C/T]TTCGAAACTGTAAACCTAAA | 141 |
| 118-85/17A5/86 | CTAAGGCGTCTCCTGAAGAA[A/G]TACAGAGAGTCGAAGAAGAT | 142 |
| 119-85/17C7/86 | CCGCGGACGACGCTTTCTTC[C/A]TCTGCTCCACCGCGAGCGC | 143 |
| 120-85/17F7/86 | GAGGAGTAGTCTCCATGGCC[G/]AAGAAGAGCGCTCGGAGACCTG | 144 |
| 121-85/17G12/86 | GAAGTTAGGGCTTCTAAGAT[C/T]AAGTTCGGCAAGGCTTTAAC | 145 |
| 122-85/18A2/86 | TCAAAACTAATATTTCTTTT[G/C]TTGATTGGTAATAAACAGGT | 146 |
| 123-85/18A11/16 | TTCCAGTGAAAAGGCATTGT[T/G]CTCCAAAATCTCGCTCTGCG | 147 |
| 124-85/18F5/86 | AAGCAGCTCTGACTTGAATG[C/A]GAGAGGTTAATCAGACTGTG | 148 |
| 125-85/18H10/86-3 | TAGATTGAAGCAATCAAGAA[G/A]ATCTCAGACTTCATCACCCA | 149 |
| 126-8 5/19B3/86 | GCATCCAACTCCAAGGATGA[/C]CCTGCCAAGGTGCTGCTAACT | 150 |
| 127-85/19C8/86 | GAGCTCAGGGATGGTGGATC[A/T]GACTACCTTGGAAAGGGTGT | 151 |
| 128-N1/19F4/N2 | TGGGGTTAGTCGAAATAGGT[A/T]AAATGCTTTGAGTATGTGTA | 152 |
| 129-N1/19H1/N2 | TACGCGCAGCACGGACTTGC[G/A]ACGCAAGCAATCGAGCTTTT | 153 |
| 130-85/20B4/86-1 | GAAGCCCATGGTACGGAGCG[G/A]GAGAGAGTCAAGTACTTGGG | 154 |
| 131-N1/20B12/N2 | AACGGGTCACTGCTAAATCA[T/A]AAGGATCACAAGGCTGGGAC | 155 |
| 132-85/20C12/86 | CTAGCCTACTTTGGGAAAAG[/T]TTCGTTATTGTTTTGTGTGG | 156 |
| 133-85/20D2/86 | GACTTCAAGGACTTCGCCGG[A/C]AAATGCTCCGACGCTGTCAA | 157 |
| 134-85/20D3/86-2 | GAGGAGGGCTACATGCAGCT[G/A]AAGAGGCTGAGGGGGCTAAA | 158 |
| 135-85/20D6/86-4 | GATGTTCAACCTATGAAGAA[G/C]AAACACCGAGGACCAACGAG | 159 |
| 136-85/20D6/86-5 | CCATTAGTGAGGGAGCATGT[T/A]CCTGTCACATTTGATGATTG | 160 |
| 137-85/20D6/86-8 | AAACACATCGCCAAAGATCC[CG/AA]ACACTCGAGAAAGAGTGGAG | 161 |
| 138-N1/20D8/N2 | CTCATAGGCGATCTGGAGTA[T/G]GCAAATCGAATCTCCTCTCC | 162 |
| 139-N1/20E1/N2 | TGCACGCCTCACTTGTTCCT[T/A]CCAATCTGACATCAAGGATT | 163 |
| 140-N1/20F1/N2-1 | NGTGTTTTTGAGGTGAAAGC[A/T]ACAAATGGAGATACCTTTTT | 164 |
| 141-N1/BOC-a2/N3-2 | CCCGAGCCATTAGGACAAGA[T/C]GACTTGCCTGTTTGACCAAAC | 165 |
| 142-N1/BOC-A2/N3-1 | CCCATCTCATCCTTTCTTGA[A/G]CCGTTGAATCAAGCTCCTGG | 166 |
| 143-N1/BOC-a2/N3-3 | TACATTCTCATTGGTTGGTT[C/A]TTGGGAAATAAAGTACCAAC | 167 |
| 144-86/SC3 | GCACGCGCTAGAGTTGTTGC[C]AGAAGGAATGAACAATCTGA | 168 |
| 145-N3/SC3/N4-1 | CTTGAGACCTATAGTCCTGT[A/T]GTTCCGTTCCGCCACAGTTCG | 169 |
| 146-N3/SC3/N5-1 | CACAGTTCGTACAGTTCCTTC[A/C]CATTGCCACTGTTATGCACT | 170 |
| 147-N1/SC3/N3-1 | GAAGGCGTCCACTATCTTGA[A/G]ACCTATAGTCCTGTTGTTCG | 171 |
| 148-86/SC3/N4-1 | TCCCGGAAATCTTGCTGAAA[A/C]CGTTTACCTGCGACAACCAG | 172 |
| 149-B11/N5-1 | ATGTCTTCAAAGTGCTCTGT[T]GCAACGCACGTCCGAACAAG | 173 |

II. Analysis of Polymorphisms

A. Preparation of Samples

Polymorphisms are detected in a target nucleic acid from a plant being analyzed. Target nucleic acids can be genomic or cDNA. Many of the methods described below require amplification of DNA from target samples. This can be accomplished by e.g., PCR. See generally *PCR Technology: Principles and Applications for DNA Amplification* (ed. H. A. Erlich, Freeman Press, NY, N.Y., 1992); *PCR Protocols: A Guide to Methods and Applications* (eds. Innis, et al., Academic Press, San Diego, Calif., 1990); Mattila et al., *Nucleic Acids Res.* 19, 4967 (1991); Eckert et al., *PCR Methods and Applications* 1, 17 (1991); PCR (eds. McPherson et al., IRL Press, Oxford); and U.S. Pat. No. 4,683,202 (each of which is incorporated by reference for all purposes).

Other suitable amplification methods include the ligase chain reaction (LCR) (see Wu and Wallace, *Genomics* 4, 560 (1989), Landegren et al., *Science* 241, 1077 (1988), transcription amplification (Kwoh et al., *Proc. Natl. Acad. Sci. USA* 86, 1173 (1989)), and self-sustained sequence replication (Guatelli et al., *Proc. Nat. Acad. Sci.* USA, 87, 1874 (1990)) and nucleic acid based sequence amplification (NASBA). The latter two amplification methods involve isothermal reactions based on isothermal transcription, which produce both single stranded RNA (ssRNA) and double stranded DNA (dsDNA) as the amplification products in a ratio of about 30 or 100 to 1, respectively.

B. Detection of Polymorphisms in Target DNA

There are two distinct types of analysis depending whether a polymorphism in question has already been characterized. The first type of analysis is sometimes referred to as de novo characterization. This analysis compares target sequences in different individual plants to identify points of variation, i.e., polymorphic sites. The de novo identification of the polymorphisms of the invention is described in the Examples section. The second type of analysis is determining which form(s) of a characterized polymorphism are present in plants under test. There are a variety of suitable procedures, which are discussed in turn.

1. Allele-Specific Probes

The design and use of allele-specific probes for analyzing polymorphisms is described by e.g., Saiki et al., *Nature* 324, 163–166 (1986); Dattagupta, EP 235,726, Saiki, WO 89/11548. Allele-specific probes can be designed that hybridize to a segment of target DNA from one member of a species but do not hybridize to the corresponding segment from another member due to the presence of different polymorphic forms in the respective segments from the two members. Hybridization conditions should be sufficiently stringent that there is a significant difference in hybridization intensity between alleles, and preferably an essentially binary response, whereby a probe hybridizes to only one of the alleles. Some probes are designed to hybridize to a segment of target DNA such that the polymorphic site aligns with a central position (e.g., in a 15 mer at the 7 position; in a 16 mer, at either the 8 or 9 position) of the probe. This design of probe achieves good discrimination in hybridization between different allelic forms.

Allele-specific probes are often used in pairs, one member of a pair showing a perfect match to a reference form of a target sequence and the other member showing a perfect match to a variant form. Several pairs of probes can then be immobilized on the same support for simultaneous analysis of multiple polymorphisms within the same target sequence.

2. Tiling Arrays

The polymorphisms can also be identified by hybridization to nucleic acid arrays, some example of which are described by WO 95/11995 (incorporated by reference in its entirety for all purposes). One form of such arrays is described in the Examples section in connection with de novo identification of polymorphisms. The same array or a different array can be used for analysis of characterized polymorphisms. WO 95/11995 also describes subarrays that are optimized for detection of a variant forms of a precharacterized polymorphism. Such a subarray contains probes designed to be complementary to a second reference sequence, which is an allelic variant of the first reference sequence. The second group of probes is designed by the same principles as described in the Examples except that the probes exhibit complementarity to the second reference sequence. The inclusion of a second group (or further groups) can be particular useful for analyzing short subsequences of the primary reference sequence in which multiple mutations are expected to occur within a short distance commensurate with the length of the probes (i.e., two or more mutations within 9 to 21 bases).

3. Allele-Snecific Primers

An allele-specific primer hybridizes to a site on target DNA overlapping a polymorphism and only primes amplification of an allelic form to which the primer exhibits perfect complementarity. See Gibbs, *Nucleic Acid Res.* 17, 2427–2448 (1989). This primer is used in conjunction with a second primer which hybridizes at a distal site. Amplification proceeds from the two primers leading to a detectable product signifying the particular allelic form is present. A control is usually performed with a second pair of primers, one of which shows a single base mismatch at the polymorphic site and the other of which exhibits perfect complementarity to a distal site. The single-base mismatch prevents amplification and no detectable product is formed. The method works best when the mismatch is included in the 3'-most position of the oligonucleotide aligned with the polymorphism because this position is most destabilizing to elongation from the primer. See, e.g., WO 93/22456.

4. Direct-Seguencing

The direct analysis of the sequence of polymorphisms of the present invention can be accomplished using either the dideoxy chain termination method or the Maxam Gilbert method (see Sambrook et al., *Molecular Cloning, A Laboratory Manual* (2nd Ed., CSHP, New York 1989); Zyskind et al., *Recombinant DNA Laboratory Manual*, (Acad. Press, 1988)).

5. Denaturing Gradient Gel Electrophoresis

Amplification products generated using the polymerase chain reaction can be analyzed by the use of denaturing gradient gel electrophoresis. Different alleles can be identified based on the different sequence-dependent melting properties and electrophoretic migration of DNA in solution. Erlich, ed., *PCR Technology, Principles and Applications for DNA Amplification*, (W. H. Freeman and Co, New York, 1992), Chapter 7.

6. Single-Strand Conformation Polymorphism Analysis

Alleles of target sequences can be differentiated using single-strand conformation polymorphism analysis, which identifies base differences by alteration in electrophoretic migration of single stranded PCR products, as described in Orita et al., *Proc. Nat. Acad. Sci.* 86, 2766–2770 (1989). Amplified PCR products can be generated as described above, and heated or otherwise denatured, to form single stranded amplification products. Single-stranded nucleic acids may refold or form secondary structures which are partially dependent on the base sequence. The different electrophoretic mobilities of single-stranded amplification products can be related to base-sequence difference between alleles of target sequences.

III. Methods of Use

After determining polymorphic form(s) present in a subject plant at-one or more polymorphic sites, this information can be used in a number of methods.

A. Fingerprint Analysis

Analysis of which polymorphisms are present in a plant is useful in determining of which strain the plant is a member an in distinguishing one strain from another. A genetic fingerprint for an individual strain can be made by determining the nucleic acid sequence possessed by that individual strain that corresponds to a region of the genome known to contain polymorphisms. For a discussion of genetic fingerprinting in the animal kingdom, see, for example, Stokening et. al., *Am. J. Hum. Genet.* 48:370–382 (1991). The probability that one or more polymorphisms in an individual strain is the same as that in any other individual strain decreases as the number of polymorphic sites is increased.

The comparison of the nucleic acid sequences from two strains at one or multiple polymorphic sites can also demonstrate common or disparate ancestry. Since the polymorphic sites are within a large region in the genome, the probability of recombination between these polymorphic sites is low. That low probability means the haplotype (the set of all the disclosed polymorphic sites) set forth in this application should be inherited without change for at least several generations. Knowledge of plant strain or ancestry is useful, for example, in a plant breeding program or in tracing progeny of a proprietary plant. Fingerprints are also used to identify an individual strain and to distinguish or determine the relatedness of one individual strain to another. Genetic fingerprinting can also be useful in hybrid certification, the certification of seed lots, and the assertion of plant breeders rights tinder the laws of various countries.

B. Correlation of Polymorphisms with Phenotypic Traits

The polymorphisms of the invention may contribute to the phenotype of a plant in different ways. Some polymorphisms occur within a protein coding sequence and contribute to phenotype by affecting protein structure. The effect may be neutral, beneficial or detrimental, or both beneficial and detrimental, depending on the circumstances. Other polymorphisms occur in noncoding regions but may exert phenotypic effects indirectly via influence on replication, transcription, and translation. A single polymorphism may affect more than one phenotypic trait. Likewise, a single phenotypic trait may be affected by polymorphisms in different genes. Further, some polymorphisms predispose a plant to a distinct mutation that is causally related to a certain phenotype.

Phenotypic traits include characteristics such as growth rate, crop yield, crop quality, resistance to pathogens, herbicides, and other toxins, nutrient requirements, resistance to high temperature, freezing, drought, requirements for light and soil type, aesthetics, and height. Other phenotypic traits include susceptibility or resistance to diseases, such as plant cancers. Often polymorphisms occurring within the same gene correlate with the same phenotype.

Correlation is performed for a population of plants, which have been tested for the presence or absence of a phenotypic trait of interest and for polymorphic markers sets. To perform such analysis, the presence or absence of a set of polymorphisms (i.e. a polymorphic set) is determined for a set of the plants, some of whom exhibit a particular trait, and some of which exhibit lack of the trait. The alleles of each polymorphism of the set are then reviewed to determine whether the presence or absence of a particular allele is associated with the trait of interest. Correlation can be performed by standard statistical methods such as a κ-squared test and statistically significant correlations between polymorphic form(s) and phenotypic characteristics are noted.

Correlations between characteristics and phenotype are useful for breeding for desired characteristics. By analogy, Beitz et al., U.S. Pat. No. 5,292,639 discuss use of bovine mitochondrial polymorphisms in a breeding program to improve milk production in cows. To evaluate the effect of mtDNA D-loop sequence polymorphism on milk production, each cow was assigned a value of 1 if variant or 0 if wildtype with respect to a prototypical mitochondrial DNA sequence at each of 17 locations considered. Each production trait was analyzed individually with the following animal model:

$$Y_{ijkpn} = \mu + YS_i + P_j + X_k + \beta_1 + \ldots \beta_{17} + PE_n + a_n + e_p$$

where $Y_{ijknp}$ is the milk, fat, fat percentage, SNF, SNF percentage, energy concentration, or lactation energy record; $\mu$ is an overall mean; $YS_i$ is the effect common to all cows calving in year-season; $X_k$ is the effect common to cows in either the high or average selection line; $\beta_1$ to $\beta_{17}$ are the binomial regressions of production record on mtDNA D-loop sequence polymorphisms; $PE_n$ is permanent environmental effect common to all records of cow n; $a_n$ is effect of animal n and is composed of the additive genetic contribution of sire and dam breeding values and a Mendelian sampling effect; and $e_p$ is a random residual. It was found that eleven of seventeen polymorphisms tested influenced at least one production trait. Bovines having the best polymorphic forms for milk production at these eleven loci are used as parents for breeding the next generation of the herd.

One can test at least several hundreds of markers simultaneously in order to identify those linked to a gene or chromosomal region. For example, to identify markers linked to a gene conferring disease resistance, a DNA pool is constructed from plants of a segregating population that are resistant and another pool is constructed from plants that are sensitive to the disease. Those two DNA pools are identical except for the DNA sequences at the resistance gene locus and in the surrounding genomic area. Hybridization of such DNA pools to the DNA sequences listed in Table 1 allows the simultaneous testing of several hundreds of loci for polymorphisms. Allelic polymorphism-detecting sequences that show differences in hybridization patterns between such DNA pools will represent loci linked to the disease resistance gene.

The method just described can also be applied to rapidly identify rare alleles in large populations of plants. For example, nucleic acid pools are constructed from several individuals of a large population. The nucleic acid pools are hybridized to nucleic acids having the polymorphism-detecting sequences listed in Table 1. The detection of a rare hybridization profile will indicate the presence of a rare allele in a specific nucleic acid pool. RNA pools are particularly suited to identify differences in gene expression.

IV. Modified Polypeptides and Gene Sequences

The invention further provides variant forms of nucleic acids and corresponding proteins. The nucleic acids comprise at least 10 contiguous amino acids of one of the sequences described in Table 1, in any of the allelic forms shown. Some nucleic acid encode full-length proteins.

Genes can be expressed in an expression vector in which a gene is operably linked to a native or other promoter. Usually, the promoter is a eukaryotic promoter for expression in a eukaryotic cell. The transcription regulation sequences typically include a heterologous promoter and optionally an enhancer which is recognized by the host. The selection of an appropriate promoter, for example trp, lac, phage promoters, glycolytic enzyme promoters and tRNA promoters, depends on the host selected. Commercially available expression vectors can be used. Vectors can include host-recognized replication systems, amplifiable genes, selectable markers, host sequences useful for insertion into the host genome, and the like.

The means of introducing the expression construct into a host cell varies depending upon the particular construction and the target host. Suitable means include fusion, conjugation, transfection, transduction, electroporation or injection, as described in Sambrook, supra. A wide variety of host cells can be employed for expression of the variant gene, both prokaryotic and eukaryotic. Suitable host cells include bacteria such as *E. coli*, yeast, filamentous fungi, insect cells, mammalian cells, typically immortalized, e.g., mouse, CHO, human and monkey cell lines and derivatives thereof, and plant cells. Preferred host cells are able to process the variant gene product to produce an appropriate mature polypeptide. Processing includes glycosylation, ubiquitination, disulfide bond formation, general post-translational modification, and the like.

The DNA fragments are introduced into cultured plant cells by standard methods including electroporation (From et al., *Proc. Natl Acad. Sci. USA* 82, 5824 (1985), infection by viral vectors such as cauliflower mosaic virus (CaMV) (Hohn et al., *Molecular Biology of Plant Tumors*, (Academic Press, New York, 1982) pp. 549–560; Howell, U.S. Pat. No. 4,407,956), high velocity ballistic penetration by small particles with the nucleic acid either within the matrix of small beads or particles, or on the surface (Klein et al., *Nature* 327, 70–73 (1987)), use of pollen as vector (WO 85/01856), or use of *Agrobacterium tumefaciens* transformed with a Ti plasmid in which DNA fragments are cloned. The Ti plasmid is transmitted to plant cells upon infection by *Agrobacterium tumefaciens*, and is stably integrated into the plant genome (Horsch et al., *Science*, 233, 496–498 (1984); Fraley et al., *Proc. Natl. Acad. Sci. USA* 80, 4803 (1983)).

The protein may be isolated by conventional means of protein biochemistry and purification to obtain a substantially pure product, i.e., 80, 95 or 99% free of cell component contaminants, as described in Jacoby, *Methods in Enzymology* Volume 104, Academic Press, New York (1984); Scopes, *Protein Purification, Principles and Practice*, 2nd Edition, Springer-Verlag, New York (1987); and Deutscher (ed), *Guide to Protein Purification, Methods in Enzymology*, Vol. 182 (1990). If the protein is secreted, it can be isolated from the supernatant in which the host cell is grown. If not secreted, the protein can be isolated from a lysate of the host cells.

The invention further provides transgenic plants capable of expressing an exogenous variant gene and/or having one or both alleles of an endogenous variant gene inactivated. Plant regeneration from cultural protoplasts is described in Evans et al., "Protoplasts Isolation and Culture," *Handbook of Plant Cell Cultures* 1, 124–176 (MacMillan Publishing Co., New York, 1983); Davey, "Recent Developments in the Culture and Regeneration of Plant Protoplasts," *Protoplasts*, (1983)—pp. 12–29, (Birkhauser, Basal 1983); Dale, "Protoplast Culture and Plant Regeneration of Cereals and Other Recalcitrant Crops," *Protoplasts* (1983)—pp. 31–41, (Birkhauser, Basel 1983); Binding, "Regeneration of Plants," Plant Protoplasts, pp. 21–73, (CRC Press, Boca Raton, 1985). For example, a variant gene responsible for a disease-resistant phenotype can be introduced into the plant to simulate that phenotype. Expression of an exogenous variant gene is usually achieved by operably linking the gene to a promoter and optionally an enhancer. Inactivation of endogenous variant genes can be achieved by forming a transgene in which a cloned variant gene is inactivated by insertion of a positive selection marker. See Capecchi, *Science* 244, 1288–1292 (1989). Such transgenic plants are useful in a variety of screening assays. For example, the transgenic plant can then be treated with compounds of interest and the effect of those compounds on the disease resistance can be monitored. In another example, the transgenic plant can be exposed to a variety of environmental conditions to determine the effect of those conditions on the resistance to the disease.

In addition to substantially full-length polypeptides, the present invention includes biologically active fragments of the polypeptides, or analogs thereof, including organic molecules which simulate the interactions of the peptides. Biologically active fragments include any portion of the full-length polypeptide which confers a biological function on the variant gene product, including ligand binding, and antibody binding. Ligand binding includes binding by nucleic acids, proteins or polypeptides, small biologically active molecules, or large cellular structures.

Polyclonal and/or monoclonal antibodies that specifically bind to one allelic gene products but not to a second allelic gene product are also provided. Antibodies can be made by injecting mice or other animals with the variant gene product or synthetic peptide fragments thereof. Monoclonal antibodies are screened as are described, for example, in Harlow & Lane, *Antibodies, A Laboratory Manual*, Cold Spring Harbor Press, New York (1988); Goding, *Monoclonal antibodies, Principles and Practice* (2d ed.) Academic Press, New York (1986). Monoclonal antibodies are tested for specific immunoreactivity with a variant gene product and lack of immunoreactivity to the corresponding prototypical gene product. These antibodies are useful in diagnostic assays for detection of the variant form, or as an active ingredient in a pharmaceutical composition.

V. Kits

The invention further provides kits comprising at least one allele-specific oligonucleotide as described above. Often, the kits contain one or more pairs of allele-specific oligonucleotides hybridizing to different forms of a polymorphism. In some kits, the allele-specific oligonucleotides are provided immobilized to a substrate. For example, the same substrate can comprise allele-specific oligonucleotide probes for detecting at least 10, 100 or all of the polymorphsms shown in Table 1. Optional additional components of the kit include, for example, restriction enzymes, reverse-transcriptase or polymerase, the substrate nucleoside triphosphates, means used to label (for example, an avidin-enzyme conjugate and enzyme substrate and chromogen if the label is biotin), and the appropriate buffers for reverse transcription, PCR, or hybridization reactions. Usually, the kit also contains instructions for carrying out the methods.

EXAMPLES

As noted above, the sequences in Table 1 were isolated from *B. napus* and *B. oleracea* using oligonucleotide primers designed from expressed DNA sequences from *Arabidopsis thaliana*, a relative of *Brassica napus* and member of the Cruciferae family. Primers used to amplify *B. napus* and *B. oleracea* alleles were selected for an optimal length of 20 bases±2 based such that their melting temperatures were between 60° C. and 65° C. Primers were synthesized on a 20 nmole scale using a high throughput DNA synthesizer capable of producing 96 primers simultaneously in a 96-well format. See Lashkari et al., *Proc. Nat. Acad. Sci.* 92, 7912–7915 (1995). The primers, which have an average length of 21 bases, were positioned within DNA sequences such that PCR products produced with cDNA templates would range between 100 and 450 bp. As introns in Arabidopsis genes are of modest size, 60% of the 1,920 primers tested on plant DNA gave PCR products.

The components needed for PCR amplification were mixed in the following proportions for a 96 well microamp tray assembly: 206:1 of 10×PCR reaction buffer, 206:1 of 2 mM dNTPs, 186:1 of 15 mM $MgCl_2$, 720:1 of sterile $ddH_2O$ and, 20:1 of Taq DNA polymerase (Perkin Elmer). The enzyme was added just prior to dispensing 168:1 of this master mix into 8 tubes. 20:1 of the appropriate forward and reverse primer 10 pmol/l stock solutions was added to each tube. A volume of 14:1 of this mixture was dispensed into each well of the microamp assembly with a BioHit 8-channel pipette. A volume of 5:1 of 20 ng/l template DNA solutions was added to the microamp assembly with a 12-channel pipette. The assembly was centrifuged for 30 sec to ensure that all reagents were mixed. Amplifications were performed in a Perkin Elmer system 9600 thermal cycler with an initial denaturation at 95° C. for 1 min followed by 40 cycles of 94° C. for 30 sec, 55° C. for 30 sec, 72° C. for 30 sec and a final extension at 72° C. for 5 min. Products were separated by electrophoresis at 120 volts for 1 hr through 2% (w/v) agarose gels prestained with ethidium bromide. The banding patterns of these gels were recorded with an Alpha Innotech gel documentation system.

Any two amplicons obtained from the same primer set with two different plant varieties are said to be homomorphic if they have the same size. A set of 355 homomorphic *Brassica napus* and 250 homomorphic *Brassica oleracae* fragments were purified with Quiaquick columns and sequenced using dye labeled dideoxy-terminators. See Stryer, *Biochemistry* 2nd. ed., pp. 592–593 (1981). The same primers used for the PCR amplification of the homomorphic DNA fragments were also used for the DNA sequencing of these fragments. The sequences obtained were aligned to identify single nucleotide polymorphisms.

Using VLSIPS™ technology (U.S. Pat. No. 5,143,854; WO 90/15070; WO 92/10092), GeneChipJ was constructed using 20mer-probe sets to identify by hybridization the presence or absence of many of the polymorphisms shown in Table 1 in a sample of plant nucleic acid. The tiling strategy used to create the GeneChipJ is set forth in FIG. 1. Tiling strategies can be devised using the guidance provided herein by those skilled in the art. Tiling arrays are described in PCT/US94/12305 (incorporated by reference in its entirety for all purposes). ATiling@ generally means the synthesis of a defined set of oligonucleotide probes that is made up of a sequence complementary to the sequence to be analyzed (the target sequence), as well as preselected variations of that sequence. The variations usually include substitution at one or more base positions with one or more nucleotides. Tiling strategies are discussed in Published PCT Application No. WO 95/11995 (incorporated by reference in its entirety for all purposes). In general, with a tiled array containing 4L probes one can query every position in a nucleotide containing L number of bases. A 4L tiled array, for example, contains L number of sets of 4 probes, i.e. 4L probes. Each set of 4 probes contains the perfect complement to a portion of the target sequence with a single substitution for each nucleotide at the same position in the probe. See also Chee, M., et. al., Science, October, 1996.

The tiling strategy for 20mer probes shown in FIG. 1 for a single allele of the polymorphism employed probe sets having a perfect match and a corresponding single-base mismatch at the tenth base in the probe, counting from the 3=end. Each set had 14 pairs of probes that began at 14 successively shifted positions such that the substituted base lay from 7 bases upstream to 6 bases downstream from the polymorphic site. Two such sets of 28 probes were included to query the polymorphic site for the two alleles, as shown for example, in FIG. 1. This collection of 56 probes constituted a detection block. Two such blocks per marker were synthesized to query both the forward and reverse strands. Thus each marker interrogated by the GeneChipJ was represented by a full set of 112 probes.

All publications and patent applications cited above are incorporated by reference in their entirety for all purposes to the same extent as if each individual publication or patent application were specifically and individually indicated to be so incorporated by reference. Although the present invention has been described in some detail by way of illustration and example for purposes of clarity and understanding, it will be apparent that certain changes and modifications may be practiced within the scope of the appended claims.

What is claimed is:

1. A nucleic acid segment comprising at least 10 contiguous nucleotides from a sequence shown in SEQ ID NOS:40, 42–44, 46, 47, 49–51, or 56 of Table 1 including a polymorphic site; or the complement of the segment.

2. The nucleic acid segment of claim 1, wherein the segment is less than 100 bases.

3. The nucleic acid segment of claim 1 that is DNA.

4. The nucleic acid segment of claim 1 that is RNA.

5. The segment of claim 1 that is less than 50 bases.

6. The segment of claim 1 that is less than 20 bases.

7. The segment of claim 1, wherein the polymorphic site is diallelic.

8. An allele-specific oligonucleotide that hybridizes to a sequence shown in Table 1 or its complement.

9. The allele-specific oligonucleotide of claim 8 that is a probe.

10. The allele-specific oligonucleotide of claim 9, wherein the a central position of the probe aligns with the polymorphic site in the sequence.

11. The allele-specific oligonucleotide of claim 8 that is a primer.

12. The allele-specific oligonucleotide of claim 11, wherein the 3' end of the primer aligns with the polymorphic site of the segment.

13. A method of analyzing a nucleic acid, comprising:

obtaining the nucleic acid from the subject; and determining a base occupying any one of the polymorphic sites shown in SEQ ID NOS:40, 42–44, 46, 47, 49–51, or 56 of Table 1.

14. The method of claim 13, wherein the determining comprises determining a set of bases occupying a set of the polymorphic sites shown in SEQ ID NOS:40, 42–44, 46, 47, 49–51, or 56 of Table 1.

15. The method of claim 13, wherein the nucleic acid is obtained from a plurality of subjects, and a base occupying one of the polymorphic positions is determined in each of the subjects, and the method further comprises testing each subject for the presence of a phenotype, and correlating the presence of the phenotype with the base.

* * * * *

UNITED STATES PATENT AND TRADEMARK OFFICE
CERTIFICATE OF CORRECTION

PATENT NO. : 6,358,686 B1
DATED : March 19, 2002
INVENTOR(S) : Lemieux et al.

It is certified that error appears in the above-identified patent and that said Letters Patent is hereby corrected as shown below:

Title page,
Item [75], Inventors, please add -- Alain Murigneux, Aubiere, FR --.

Column 75,
Lines 26-28, please amend claim 10 as follows:

-- The allele-specific oligonucleotide of claim 9, wherein a central position of the probe aligns with the polymorphic site in the sequence. --

Signed and Sealed this

Third Day of June, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,358,686 B1  Page 1 of 5
DATED : March 19, 2002
INVENTOR(S) : Lemieux et al.

It is certified that error appears in the above-identified patent and that said Letters Patent is hereby corrected as shown below:

<u>Columns 5-8,</u>
Table 1, please amend as follows:

| Marker Name | Sequence | SEQ ID NO |
|---|---|---|
| 1-85/5B5/86-1 | AGCAAGCTTACATGCGTGGA[GT/AA]GAGAGTCCTCGAGATCAACC | 30 |
| 2-85/5B12/N3-1 | CCTTGATCTCTCAAGTAATC[A/G]TCTCACCGGAAGATCCCTGA | 31 |
| 3-85/5C3/86-2 | ACCATCCATTAAACTGTATC[A/G]TCGCAATCTAACCAAAAGTT | 32 |
| 4-85/5E1/86-1 | TAAAGCAAAGAGAGTCTTAC[C/A]GTCTGCTGCATGATATACCC | 33 |
| 5-85/5E1/86-2 | CTACTGATAGTGAACCACCC[A/C]ATCCCCAAATTTAAAGCAAA | 34 |
| 6-85/6A11/86 | ATCCTATTGGTAGTAACACA[G/A]ATTGAGTTAATGTTGCAGGG | 35 |
| 7-N1/6A11/N2 | AGGCAAAGCGGTAGTTGCAA[G/A]ACTGCTTCTCACGAGGTAAT | 36 |
| 8-N1/6A9/N2-1 | CCAGCTTCAATGTCTGCATG[C/A]TTGTGTCGATGCCAAAGTTC | 37 |
| 9-N1/6A9/N2-2 | AAAGTTCATTACGATGATCT[A/G]ACCCTGCAGTCATCCATGGA | 38 |
| 10-85/6A12/86 | CTTCCCCCCCTCAATACCTC[T/G]TTCAAAAGTGAAAAGTGCAG | 39 |
| 11-N1/6D1/N2-1 | ATTTTGTTTTGTTTCTTGTC[G/C]GGTCAGGTCAGAACAAAGTT | 40 |
| 12-N1/6H5/N2 | AAACCAGAGCCACCTCCTTA[C/]CCACCTCATCGTTTCCTTTC | 41 |
| 13-86/6F11/N2-2 | GATTTCGACCGCAGTCTCAC[G/T]GAGGATGAGTATATCGCTTT | 42 |
| 14-N1/6F11/N2 | TAGGACAGGCAAACAATCTA[C/A]GCGGTCAAAATCCGATTTCG | 43 |
| 16-N1/8B5/N2 | ACTCAAAAAAACGATACCTC[G/C]GCCGTCTCTCGCCGTCTCGC | 44 |
| 17-N1/8D4/N2-1 | CAGGAGACAGTTACAGTCCC[/A]CAGAGTCGCAAGGATCTCGAA | 45 |
| 18-85/8D4/86-2 | CTGATCTTGAAGGAGAGACC[A/G]CCACAAGGTTCCATCCTATG | 46 |
| 19-85/8H11/86 | AGTGCgAGGCTCAGTTGGAT[G/T]ATTAGGGTGTCAGTAAATCA | 47 |
| 20-85/10B8/86 | NAGGTCCATGATGATGACAA[T/A]AAAGGTATTCCACATGTCAA | 48 |
| 21-N2/10B8/N3-2 | ACATCCAACTTTTCTCCAGT[T/C]CTTTATTCTATCCTGATTTG | 49 |
| 22-N2/10B8/N3-1 | AAGGTATTCCATTGGTATAC[A/C]TCCAACTTTTCTCCAGTTCT | 50 |
| 23-85/10B9/86 | GACCTTCTTGGGAAAGAAAG[T/C]TGTAACCGCGTCGAGATTCG | 51 |
| 24-10C8/N2 | ATAGAAACCGCCGATGCTCA[A]GGACACGCCACCGTCTTCGT | 52 |
| 25-10C8/N2 | CACTTTCTTCGTGGCTAAAT[T]CTTCGGCCGAGCCGGTCTCA | 53 |
| 26-10D2/N1 | GTTATCATCAGTACCGGTAT[T]AACCCCAAGGCTAATTCTTA | 54 |
| 27-85/10D2 | TTGGGTATCTACGGACTGAT[C]ATCGCTGTTATCATCAGTAC | 55 |
| 28-N1/10E12/N2-1 | GGAATTCAATACTCGCCAAC[G/T]TCTTCATTGCTGTCGTCGGC | 56 |

UNITED STATES PATENT AND TRADEMARK OFFICE
CERTIFICATE OF CORRECTION

PATENT NO. : 6,358,686 B1  Page 2 of 5
DATED : March 19, 2002
INVENTOR(S) : Lemieux et al.

It is certified that error appears in the above-identified patent and that said Letters Patent is hereby corrected as shown below:

Columns 5-8 (cont'd),

| | | |
|---|---|---|
| 29-N1/10E12/N2-2 | TCCTTACGCCTTCAAGCGCA[C/G]CGGCTGGCTCATGGGTGTCC | 57 |
| 30-N1/10F4/N2 | TGTATCTATGCGGTGGCTGC[G/C]GTCTCCGTTCGCGCCAGTAC | 58 |
| 31-10F4/N2 | GCGCCAGTACCGCCGGTTAC[A]ATCTcACTGCCTTCACGTCC | 59 |
| 32-85/10F4/N2 | GCGCCAGTACCGCCGGTTAC[G/A]ATCTTAATGCCTTCACGTTC | 60 |
| 33-85/10F9/N1-2 | AACTTGGAATTCCACAACTT[G/C]AGAAACTTCGATGTGGTGCC | 61 |
| 34-85/10F9/86 | CGGTACTGCGAAAGCTGGAG[C/G]ATCAACTTGGAATTCCACAA | 62 |
| 35-86/10F12 | AAAAGTGCTATTGTTCAGGT[G]GATGCTGCTCCGTTCAAGCA | 63 |
| 36-85/10H6/86 | GTCAAAAGCCACGGATTCAA[G/A]AACGTGCTCTTCTTGCGCCT | 64 |
| 38-85/10F12/86 | AAACCAGGGTCCTTGATGTG[T/]GTCTACAACGCTTCCAACAA | 65 |
| 39-85/11B7/86 | AANACCCTGAGCTCATGCCT[C/T]TGACCCATGTTCTTGCCACC | 66 |
| 40-85/11C4/86 | TTTGGGACCGTTGGAGTTGC[A/G]TCTGCGGCTATGACGGTGGA | 67 |
| 41-85/11D4/86-2 | AATCTTTGCCATTGCTGTCA[A/G]TATCTTCGTCAGCTTCAGCT | 68 |
| 43-N2/11D11/N3 | GACAACGCTGGTGGTATTGC[C/T]GAAATGGCTGGAATGAGCCA | 69 |
| 44-86/11D11/N3 | GCTGCTCTAGGGATGCTCAG[C/T]ACCATCGCCACCGGTTTGGC | 70 |
| 45-85/11D11/86 | ATGCTCAGCACCATCGCCAC[T/C]GGTTTgGCGATTGATGCTTA | 71 |
| 46-N2/11E3/N8a | GAGAAAGTGCTTGTGGAGAT[C/T]TACAaGTCCATACTGATGGC | 72 |
| 47-86/11E3/N2a | AATGCTTGTGGAGATtTACA[G/A]GTCCATACTGATGGCGCAGG | 73 |
| 48-86/11E3/N2b | AATGCTTGTGGAGATcTACA[G/A]GTCCATACTGATGGCGCAGG | 74 |
| 49-85/11F12/86 | AATGATTGGTTTGAGAAGCA[T/A]ACAGCTGGTACGCTTGATAT | 75 |
| 50-85/11F7/86 | GATAGGGCGAAGAGAGGGAA[G/A]AGTCCTGAGAGGAAAGAGAT | 76 |
| 51-85/11H2/86-2 | CTCTCTCTCCACAAAGACAC[A/C]GCTTTCTCCATGACCTTCGG | 77 |
| 52-85/11H5/86-2 | TCTCTGACGTCATGAAAGCT[C/A]ATGGCAAAATTGCTGATGGA | 78 |
| 53-85/11H6/86-1a | GTTATCGATCGCGTGGTCCG[T/C]GAAACCCAAAATaCACCTTT | 79 |
| 54-85/11H6/86-1b | GTTATCGATCGCGTGGTCCG[T/C]GAAACCCAAAATtCACCTTT | 80 |
| 55-85/12B6/N3 | CGTCAGCCTTCTTCCGCCGC[A/C]GTCGTCCTCCGCAACCGTGC | 81 |
| 56-86/12B6/85a | TGTCTCTTCCGTCAGCCTTC[C/T]TCCGCCGCAGTCGTCCTCCG | 82 |
| 57-86/12B6/85b | TGTCTCTTCCGTCAGCCTTC[C/T]TCCGCCGCcGTCGTCCTCCG | 83 |
| 58-86/12B11/85 | TCAGGTTTACCTCTATATAT[T/]ATATTTCATGGTATGAAGGT | 84 |
| 59-n1/12B11/N2-2 | TATCCTGCAAATTGACATTT[T/C]CCTTCAGGTTCTAGAAGCTG | 85 |
| 60-85/12C2/86 | CGAGAACAGAAGAGAAGAGA[C/]TGGAACACGTCGGACAGTAC | 86 |
| 62-12C11/N2 | ACGGGTCCTAGCGCCATGGC[T]ATTTTCCTCACCGTTTCTGG | 87 |
| 63-N1/12D10 | TTGGGCTTTCGGTGGTATGA[T]CTTCGTCCTCGTCTATTGCA | 88 |
| 65-85/12F4/86-1 | TCCTTGATTCCTTAATAATC[A/T]TTGGCTGGGGGTCTTTCTAA | 89 |
| 66-12G5/N1 | GCTTGAATAACGATGTCTAC[T]CTGCCTCGGCGTACGGCGGA | 90 |
| 67-85/12G8 | CTAAAAAGATCGACGAGTGT[C]CCTTACTACGCTCCATCTAT | 91 |
| 68-12G9/N1-1 | AGGTGGGTTTAGCGTGGCAT[C]CGATCCATTGGATGGATCCA | 92 |
| 69-85/12G9/ | NGTGGGTTTACCGTATCATT[T]GATCCATTGGATGGATCGAG | 93 |
| 70-12B11/N2-1 | GCGGATCCTATATTGGGTCT[T]GATGGATTGTTTCTATCCCG | 94 |
| 71-/12B11/N2-2 | TATCCTGCAAATTGACATTT[C]CCTTCAGGTTCTAGAAGCTG | 95 |
| 72-N1/12E10 | TACCACGGTCGTACTGGTCG[A]TGTCTGGAACGTCACCAAGC | 96 |
| 73-N1/13A3/N2a | CTGTCTCAgTTTGTTGGATC[C/G]AAATCgAATCGAAAGCGTAC | 97 |
| 74-N1/13A3/N2b | CTGTCTCAgTTTGTTGGATC[C/G]AAATCaAATCGAAAGCGTAC | 98 |

UNITED STATES PATENT AND TRADEMARK OFFICE
CERTIFICATE OF CORRECTION

PATENT NO. : 6,358,686 B1  
DATED : March 19, 2002  
INVENTOR(S) : Lemieux et al.

Page 3 of 5

It is certified that error appears in the above-identified patent and that said Letters Patent is hereby corrected as shown below:

Columns 5-8 (cont'd),

| | | |
|---|---|---|
| 75-13E8/N2 | ACACTGTTGGAGGACGTGAA[G]AAGATATTCAAGACAACATC | 99 |
| 76-N1/13F6/N2-2 | TCTTTCGTATCTTGCTGAGT[C/T]GTTACGCCTGTCAACACCCG | 100 |
| 77-13F8/N2-1 | GGAACCCTAGGGAGCCCACA[G]CTCCTTATGCTAAGCGGCGT | 101 |
| 78-13F8/N2 | GATCATAGTATCCGCCGGAA[C]CCTAGGGAGCCCACAGCTCC | 102 |
| 79-85/14B5/86 | TTCGGCGGGTCGATCCGGGC[A/G]GAAGACATTGTCAGGTGANN | 103 |
| 80-N1/14C2/N2 | GCACCAACATTGTAAACCTA[T/G]AGCTTCTTCCTCAGCCACCT | 104 |
| 81-85/14C2/86-1 | GCTGCCACATAGTGAACCTA[T/A]AGCTTCTTCCTCAGCCACCT | 105 |
| 82-N2/14C2/85-2 | GCACCAACATTGTGAACCTA[G/A]AGCTTCTTCCTCAGCCACCT | 106 |
| 83-85/14C2/86-2 | AGTACATAGCTATTGACTAA[C/G]TTAAGTTCCTTGTATTGTTG | 107 |
| 84-N2/14C2/85-1 | CCTCTATCCGCCATGGTTGC[A/T]CCAACATTGTGAACCTAGAG | 108 |
| 85-85/14E2/86-2 | TTGACCCTCGGCAAGCCACC[G/T]GTCAAGCCATGCTGCAGCCT | 109 |
| 86-85/14E2/86-1 | AGGCTGCCCTCTCCCAATTC[A/C]AAAGCCAACTCCTAAACCAA | 110 |
| 87-85/14E8/86 | AAACATGGAAAGGCCTGATA[/G]TCACCGTCAAGCTCACCGTC | 111 |
| 88-85/14E12/86 | CAACCTGAAAAATTGTTTTA[C/A]CAACGGCCCCGCTTTCTCCA | 112 |
| 89-14H10/86 | AAGGCCAACAACGACATTAC[C]TCCATCGTTAGCAACGGAGG | 113 |
| 90-85/14H10/86 | TCACCGGCTTGAAGTCTTCC[G/T]CTGCATTCCCAGTCACCCGC | 114 |
| 91-85/15A6/86 | ACTCAGCTTTCTTATGCCTC[G/]ACTTGCGACACACGAATCCA | 115 |
| 92-85/15C4/86 | TGCGGCTAACATCTCTGGTG[G/T]TCACCTTAACCCAGCCGTAN | 116 |
| 93-85/15E5/86-1 | CGAGGATCACTTCTCTCTGT[G/T]CAAGAAGAAGTTCGGcAAGG | 117 |
| 94-N1/15E5/N2-1 | CTGTtCAAGAAGAAGTTCGG[C/T]AAGGTCTACGCTTCCCGCGA | 118 |
| 95-N1/15E5/N2-2 | CCCTCTGCTCGTCACGGCGT[T/A]ACGCAGTTCTCGGATCTGAC | 119 |
| 96-86/15E5/N2 | CCCGCGAGGAGCACGACTAC[A/T]GATTCTCCGTTTTCAAATCC | 120 |
| 97-15E9/86 | TCCACTCGCCGGGAAGAAAC[T]CGACAAACCGTTGTCTACTT | 121 |
| 98-N2/15E9 | ATGGCTCGCGACGGGTCTCC[G]GTAAACCTCGGAGAGCAGAT | 122 |
| 99-N2/15E9/86 | GCCGACTCTCGAAGCTTCTT[A/]ACTCCACTCGCCGGGAAGAA | 123 |
| 100-85/15E9/86-1 | GAATCTAGGAGAGCAGATCT[T/G]CCTCTCTATCTTCAATGTTC | 124 |
| 101-85/15E9/86-2 | TCCACTCGCCGGGAAGAAAC[C/T]CGACAAACCGTTGTCTACAT | 125 |
| 102-N1/15E9/N2-1 | GTCATGAAGATATTCACTAC[A/G]CCGACTCTCGAAGCTTCTTA | 126 |
| 103-85/15F1/86 | GCAGGTAAAATTCTACAGAC[C/A]TTCCCTTTTCATTGTAGTTA | 127 |
| 104-85/15F5/86 | TCTCCTCCGCCGCGCAAGAA[G/A]AAATCGACAGCGGCGCGTCT | 128 |

UNITED STATES PATENT AND TRADEMARK OFFICE
CERTIFICATE OF CORRECTION

PATENT NO.   : 6,358,686 B1　　　　　　　　　　　　　　　　　　　　　Page 4 of 5
DATED        : March 19, 2002
INVENTOR(S)  : Lemieux et al.

It is certified that error appears in the above-identified patent and that said Letters Patent is hereby corrected as shown below:

Columns 5-8 (cont'd),

| | | |
|---|---|---|
| 105-85/15F10/86 | GTGCCCTAAAGATACCCTCA[A/G]GCTTGGTGTCTGCGCTAATG | 129 |
| 106-N2/15G1 | TTCTTCCCACAGGTGAAACT[T]GCTAACTTCCTTCCAAAGTA | 130 |
| 107-N1/15H7/N2 | TATGTATCAGGACAATGTGT[GA/TT]GTGACTGTGGTTGCATCCAT | 131 |
| 108-N1/16A1/N2-1 | GCTAAGCTACGCAACTGCCA[C/T]CAATCAGGGCAAGCTAAAGG | 132 |
| 109-85/16A5/86 | TATACACTCTTTAAAAGCGT[G/C]TGTGTGTACCCATCTCTCTT | 133 |
| 110-N1/16B6/N2 | ATGGCTGCGTATTGGCTGTC[C/T]AAGGCTGGATCTTGGTCCCA | 134 |
| 111-85/16B6/N1 | GGATCCATCTCAACTATGGT[A/C]GTATTATCGTTGAGGCTAGG | 135 |
| 112-85/16B7/86 | GTATGTGATTCGGAAGAGAA[T/]CAAACTAAGTGCCGAGAAAG | 136 |
| 113-N1/16D6/N2 | GCTAAGGTAGTTGGAGGAGC[CAA/GTG]CCACAGCCACGCGACTAAGG | 137 |
| 114-85/16D10/86 | CTCAACGTAGCAAGTAATAA[T/G]ATACTGTCTATTTATGGTTA | 138 |
| 115-N1/16E9/N2 | AGACTTTCCCCATTCTCTTC[T/A]CCATCCACCGTCGAAACCCA | 139 |
| 116-85/16H3/86-1 | ACTTCGAAACTGTAAACCTA[A/T]ACTTTAAGAGTTTAGAGCTA | 140 |
| 117-85/16H3/86-2 | CACCATCGGAGAAAGAGGTA[C/T]TTCGAAACTGTAAACCTAAA | 141 |
| 118-85/17A5/86 | CTAAGGCGTCTCCTGAAGAA[A/G]TACAGAGAGTCGAAGAAGAT | 142 |
| 119-85/17C7/86 | CCGCGGACGACGCTTTCTTC[C/A]TCTGCTCCACCGCGAGCGCC | 143 |
| 120-85/17F7/86 | GAGGAGTAGTCTCCATGGCC[G/]AAGAAGAGCGTCGGAGACCTG | 144 |
| 121-85/17G12/86 | GAAGTTAGGGCTTCTAAGAT[C/T]AAGTTCGGCAAGGCTTTAAC | 145 |
| 122-85/18A2/86 | TCAAAACTAATATTTCTTTT[G/C]TTGATTGGTAATAAACAGGT | 146 |
| 123-85/18A11/86 | TTCCAGTGAAAAGGCATTGT[T/G]CTCCAAAATCTCGCTCTGCG | 147 |
| 124-85/18F5/86 | AAGCAGCTCTGACTTGAATG[C/A]GAGAGGTTAATCAGACTGTG | 148 |
| 125-85/18H10/86-3 | TAGATTGAAGCAATCAAGAA[G/A]ATCTCAGACTTCATCACCCA | 149 |
| 126-85/19B3/86 | GCATCCAACTCCAAGGATGA[/C]CCTGCCAAGGTGCTGCTAACT | 150 |
| 127-85/19C8/86 | GAGCTCAGGGATGGTGGATC[A/T]GACTACCTTGGAAAGGGTGT | 151 |
| 128-N1/19F4/N2 | TGGGGTTAGTCGAAATAGGT[A/T]AAATGCTTTGAGTATGTGTA | 152 |
| 129-N1/19H1/N2 | TACGCGCAGCACGGACTTGC[G/A]ACGCAAGCAATCGAGCTTTT | 153 |
| 130-85/20B4/86-1 | GAAGCCCATGGTACGGAGCG[G/A]GAGAGAGTCAAGTACTTGGG | 154 |
| 131-N1/20B12/N2 | AACGGGTCACTGCTAAATCA[T/A]AAGGATCACAAGGCTGGGAC | 155 |
| 132-85/20C12/86 | CTAGCCTACTTTGGGAAAAG[/T]TTCGTTATTGTTTTGTGTGG | 156 |
| 133-85/20D2/86 | GACTTCAAGGACTTCGCCGG[A/C]AAATGCTCCGACGCTGTCAA | 157 |
| 134-85/20D3/86-2 | GAGGAGGGCTACATGCAGCT[G/A]AAGAGGCTGAGGGGGCTAAA | 158 |
| 135-85/20D6/86-4 | GATGTTCAACCTATGAAGAA[G/C]AAACACCGAGGACCAACGAG | 159 |
| 136-85/20D6/86-5 | CCATTAGTGAGGGAGCATGT[T/A]CCTGTCACATTTGATGATTG | 160 |
| 137-85/20D6/86-8 | AAACACATCGCCAAAGATCC[CG/AA]ACACTCGAGAAAGAGTGGAG | 161 |
| 138-N1/20D8/N2 | CTCATAGGCGATCTGGAGTA[T/G]GCAAATCGAATCTCCTCTCC | 162 |
| 139-N1/20E1/N2 | TGCACGCCTCACTTGTTCCT[T/A]CCAATCTGACATCAAGGATT | 163 |
| 140-N1/20F1/N2-1 | NGTGTTTTTGAGGTGAAAGC[A/T]ACAAATGGAGATACCTTTTT | 164 |
| 141-N1/BoC-a2/N3-2 | CCCGAGCCATTAGGACAAGA[T/C]GACTTGCCGTTTGACCAAAC | 165 |
| 142-N1/BOC-A2/N3-1 | CCCATCTCATCCTTTCTTGA[A/G]CCGTTGAATCAAGCTCCTGG | 166 |
| 143-N1/BoC-a2/N3-3 | TACATTCTCATTGGTTGGTT[C/A]TTGGGAAATAAAGTACCAAC | 167 |
| 144-86/SC3 | GCACGCGCTAGAGTTGTTGC[C]AGAAGGAATGAACAATCTGA | 168 |
| 145-N3/SC3/N4-1 | CTTGAGACCTATAGTCCTGT[A/T]GTTCGGTCCGCCACAGTTCG | 169 |
| 146-N3/SC3/N5-1 | CACAGTTCGTACAGTTCTTC[A/C]CATTGCCACTGTTATGCACT | 170 |

UNITED STATES PATENT AND TRADEMARK OFFICE
CERTIFICATE OF CORRECTION

PATENT NO. : 6,358,686 B1
DATED : March 19, 2002
INVENTOR(S) : Lemieux et al.

It is certified that error appears in the above-identified patent and that said Letters Patent is hereby corrected as shown below:

Columns 5-8 (cont'd),

| | | |
|---|---|---|
| 147-N1/SC3/N3-1 | GAAGGCGTCCACTATCTTGA[A/G]ACCTATAGTCCTGTTGTTCG | 171 |
| 148-86/SC3/N4-1 | TCCCGGAAATCTTGCTGAAA[A/C]CGTTTACCTGCGACAACCAG | 172 |
| 149-B11/N5-1 | ATGTCTTCAAAGTGCTCTGT[T]GCAACGCACGTCCGAACAAG | 173 |

Signed and Sealed this

Fourteenth Day of June, 2005

JON W. DUDAS
*Director of the United States Patent and Trademark Office*

SEQUENCE LISTING (1) GENERAL INFORMATION:

(iii) NUMBER OF SEQUENCES: 173

(2) INFORMATION FOR SEQ ID NO: 1:

(i) SEQUENCE CHARACTERISTICS:
      (A) LENGTH: 41 base pairs
      (B) TYPE: nucleic acid
      (C) STRANDEDNESS: single
      (D) TOPOLOGY: linear (xi) SEQUENCE DESCRIPTION: SEQ ID NO: 1:

TCAAAACTAA TATTTCTTTT GTTGATTGGT AATAAACAGG T          41

(2) INFORMATION FOR SEQ ID NO: 2:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 2:

TCAAAACTAA TATTTCTTTT CTTGATTGGT AATAAACAGG T                          41

(2) INFORMATION FOR SEQ ID NO: 3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 3:

TTGATTATAW AGAAAACAAC                                                  20

(2) INFORMATION FOR SEQ ID NO: 4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 4:

TTGATTATAW AGAAAGAAC                                                   20

(2) INFORMATION FOR SEQ ID NO: 5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 5:

TGATTATAAW GAAAACAACT                                                  20

(2) INFORMATION FOR SEQ ID NO: 6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 6:

TGATTATAAW GAAAGAACT                                                   20

(2) INFORMATION FOR SEQ ID NO: 7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 7:

GATTATAAAS AAAACAACTA                                                  20

(2) INFORMATION FOR SEQ ID NO: 8:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (xi) SEQUENCE DESCRIPTION: SEQ ID NO: 8:

GATTATAAAS AAAAGAACTA                                               20

(2) INFORMATION FOR SEQ ID NO: 9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 9:

ATTATAAAGW AAACAACTAA                                               20

(2) INFORMATION FOR SEQ ID NO: 10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 10:

ATTATAAAGW AAAGAACTAA                                               20

(2) INFORMATION FOR SEQ ID NO: 11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 11:

TTATAAAGAW AACAACTAAC                                               20

(2) INFORMATION FOR SEQ ID NO: 12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 12:

TTATAAAGAW AAGAACTAAC                                               20

(2) INFORMATION FOR SEQ ID NO: 13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 13:

TATAAAGAAW ACAACTAACC                                               20

(2) INFORMATION FOR SEQ ID NO: 14:

(i) SEQUENCE CHARACTERISTICS:

(A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 14:

TATAAAGAAW AGAACTAACC                                            20

(2) INFORMATION FOR SEQ ID NO: 15:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 15:

ATAAAGAAAW CAACTAACCA                                            20

(2) INFORMATION FOR SEQ ID NO: 16:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 16:

ATAAAGAAAW GAACTAACCA                                            20

(2) INFORMATION FOR SEQ ID NO: 17:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 17:

TAAAGAAAAS AACTAACCAT                                            20

(2) INFORMATION FOR SEQ ID NO: 18:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 18:

AAAGAAAACW ACTAACCATT                                            20

(2) INFORMATION FOR SEQ ID NO: 19:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 19:

AAAGAAAAGW ACTAACCATT                                            20

(2) INFORMATION FOR SEQ ID NO: 20:

(i) SEQUENCE CHARACTERISTICS:
        (A) LENGTH: 20 base pairs (B) TYPE: nucleic acid
            (C) STRANDEDNESS: single
            (D) TOPOLOGY: linear (xi) SEQUENCE DESCRIPTION: SEQ ID NO: 20:

AAGAAAACAW CTAACCATTA                                               20

(2) INFORMATION FOR SEQ ID NO: 21:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO: 21:

AAGAAAAGAW CTAACCATTA                                               20

(2) INFORMATION FOR SEQ ID NO: 22:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO: 22:

AGAAAACAAS TAACCATTAT                                               20

(2) INFORMATION FOR SEQ ID NO: 23:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO: 23:

AGAAAGAAS TAACCATTAT                                                20

(2) INFORMATION FOR SEQ ID NO: 24:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO: 24:

GAAAACAACW AACCATTATT                                               20

(2) INFORMATION FOR SEQ ID NO: 25:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO: 25:

GAAAGAACW AACCATTATT                                                20

(2) INFORMATION FOR SEQ ID NO: 26:

(i) SEQUENCE CHARACTERISTICS:
            (A) LENGTH: 20 base pairs
            (B) TYPE: nucleic acid (C) STRANDEDNESS: single
        (D) TOPOLOGY: linear (xi) SEQUENCE DESCRIPTION: SEQ ID NO: 26:

AAAACAACTW ACCATTATTT                                                           20

(2) INFORMATION FOR SEQ ID NO: 27:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 27:

AAAAGAACTW ACCATTATTT                                                           20

(2) INFORMATION FOR SEQ ID NO: 28:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 28:

AAACAACTAW CCATTATTTG                                                           20

(2) INFORMATION FOR SEQ ID NO: 29:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 29:

AAAGAACTAW CCATTATTTG                                                           20

(2) INFORMATION FOR SEQ ID NO: 30:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (xi) SEQUENCE DESCRIPTION: SEQ ID NO: 30:

AGCAAGCTTA CATGCGTGGA RWGAGAGTCC TCGAGATCAA CC                                  42

(2) INFORMATION FOR SEQ ID NO: 31:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 31:

CCTTGATCTC TCAAGTAATC RTCTCACCGG AAGATCCCTG A                                   41

(2) INFORMATION FOR SEQ ID NO: 32:

(i) SEQUENCE CHARACTERISTICS:
        (A) LENGTH: 41 base pairs
        (B) TYPE: nucleic acid
        (C) STRANDEDNESS: single (D) TOPOLOGY: linear (xi) SEQUENCE DESCRIPTION: SEQ ID NO: 32:

ACCATCCATT AAACTGTATC RTCGCAATCT AACCAAAAGT T          41

(2) INFORMATION FOR SEQ ID NO: 33:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 33:

TAAAGCAAAG AGAGTCTTAC MGTCTGCTGC ATGATATACC C          41

(2) INFORMATION FOR SEQ ID NO: 34:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 34:

CTACTGATAG TGAACCACCC MATCCCCAAA TTTAAAGCAA A          41

(2) INFORMATION FOR SEQ ID NO: 35:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 35:

ATCCTATTGG TAGTAACACA RATTGAGTTA ATGTTGCAGG G          41

(2) INFORMATION FOR SEQ ID NO: 36:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 36:

AGGCAAAGCG GTAGTTGCAA RACTGCTTCT CACGAGGTAA T          41

(2) INFORMATION FOR SEQ ID NO: 37:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 37:

CCAGCTTCAA TGTCTGCATG MTTGTGTCGA TGCCAAAGTT C          41

(2) INFORMATION FOR SEQ ID NO: 38:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 38:

AAAGTTCATT ACGATGATCT RACCCTGCAG TCATCCATGG A                41

(2) INFORMATION FOR SEQ ID NO: 39:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 39:

CTTCCCCCCC TCAATACCTC KTTCAAAAGT GAAAAGTGCA G                41

(2) INFORMATION FOR SEQ ID NO: 40:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 40:

ATTTTGTTTT GTTTCTTGTC SGGTCAGGTC AGAACAAAGT T                41

(2) INFORMATION FOR SEQ ID NO: 41:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ix) FEATURE:
        (A) NAME/KEY: variation
        (B) LOCATION: replace(21, "")
        (D) OTHER INFORMATION: /note= "deletion polymorphism"

(xi) SEQUENCE DESCRIPTION: SEQ ID NO: 41:

AAACCAGAGC CACCTCCTTA CCCACCTCAT CGTTTCCTTT C                41

(2) INFORMATION FOR SEQ ID NO: 42:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 42:

GATTTCGACC GCAGTCTCAC KGAGGATGAG TATATCGCTT T                41

(2) INFORMATION FOR SEQ ID NO: 43:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 43:

TAGGACAGGC AAACAATCTA MGCGGTCAAA ATCCGATTTC G                41

(2) INFORMATION FOR SEQ ID NO: 44:

(i) SEQUENCE CHARACTERISTICS:

(A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 44:

ACTCAAAAAA ACGATACCTC SGCCGTCTCT CGCCGTCTCG C         41

(2) INFORMATION FOR SEQ ID NO: 45:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ix) FEATURE:
        (A) NAME/KEY: variation
        (B) LOCATION: replace(21, "")
        (D) OTHER INFORMATION: /note= "deletion polymorphism"

(xi) SEQUENCE DESCRIPTION: SEQ ID NO: 45:

CAGGAGACAG TTACAGTCCC ACAGAGTCGC AAGGATCTCG AA        42

(2) INFORMATION FOR SEQ ID NO: 46:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 46:

CTGATCTTGA AGGAGAGACC RCCACAAGGT TCCATCCTAT G         41

(2) INFORMATION FOR SEQ ID NO: 47:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 47:

AGTGCGAGGC TCAGTTGGAT KATTAGGGTG TCAGTAAATC A         41

(2) INFORMATION FOR SEQ ID NO: 48:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 48:

NAGGTCCATG ATGATGACAA WAAAGGTATT CCACATGTCA A         41

(2) INFORMATION FOR SEQ ID NO: 49:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 49:

ACATCCAACT TTTCTCCAGT YCTTTATTCT ATCCTGATTT G         41

(2) INFORMATION FOR SEQ ID NO: 50:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 50:

AAGGTATTCC ATTGGTATAC MTCCAACTTT TCTCCAGTTC T            41

(2) INFORMATION FOR SEQ ID NO: 51:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 51:

GACCTTCTTG GGAAAGAAAG YTGTAACCGC GTCGAGATTC G            41

(2) INFORMATION FOR SEQ ID NO: 52:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 52:

ATAGAAACCG CCGATGCTCA AGGACACGCC ACCGTCTTCG T            41

(2) INFORMATION FOR SEQ ID NO: 53:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 53:

CACTTTCTTC GTGGCTAAAT TCTTCGGCCG AGCCGGTCTC A            41

(2) INFORMATION FOR SEQ ID NO: 54:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 54:

GTTATCATCA GTACCGGTAT TAACCCCAAG GCTAATTCTT A            41

(2) INFORMATION FOR SEQ ID NO: 55:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 55:

TTGGGTATCT ACGGACTGAT CATCGCTGTT ATCATCAGTA C            41

(2) INFORMATION FOR SEQ ID NO: 56:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 56:

GGAATTCAAT ACTCGCCAAC KTCTTCATTG CTGTCGTCGG C          41

(2) INFORMATION FOR SEQ ID NO: 57:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 57:

TCCTTACGCC TTCAAGCGCA SCGGCTGGCT CATGGGTGTC C          41

(2) INFORMATION FOR SEQ ID NO: 58:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 58:

TGTATCTATG CGGTGGCTGC SGTCTCCGTT CGCGCCAGTA C          41

(2) INFORMATION FOR SEQ ID NO: 59:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 59:

GCGCCAGTAC CGCCGGTTAC AATCTCACTG CCTTCACGTC C          41

(2) INFORMATION FOR SEQ ID NO: 60:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 60:

GCGCCAGTAC CGCCGGTTAC RATCTTAATG CCTTCACGTT C          41

(2) INFORMATION FOR SEQ ID NO: 61:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 61:

AACTTGGAAT TCCACAACTT SAGAAACTTC GATGTGGTGC C          41

(2) INFORMATION FOR SEQ ID NO: 62:

(i) SEQUENCE CHARACTERISTICS:
    (A) LENGTH: 41 base pairs
    (B) TYPE: nucleic acid
    (C) STRANDEDNESS: single
    (D) TOPOLOGY: linear (xi) SEQUENCE DESCRIPTION: SEQ ID NO: 62:

CGGTACTGCG AAAGCTGGAG SATCAACTTG GAATTCCACA A            41

(2) INFORMATION FOR SEQ ID NO: 63:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 63:

AAAAGTGCTA TTGTTCAGGT GGATGCTGCT CCGTTCAAGC A            41

(2) INFORMATION FOR SEQ ID NO: 64:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 64:

GTCAAAAGCC ACGGATTCAA RAACGTGCTC TTCTTGCGCC T            41

(2) INFORMATION FOR SEQ ID NO: 65:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ix) FEATURE:
        (A) NAME/KEY: variation
        (B) LOCATION: replace(21, "")
        (D) OTHER INFORMATION: /note= "deletion polymorphism"

(xi) SEQUENCE DESCRIPTION: SEQ ID NO: 65:

AAACCAGGGT CCTTGATGTG TGTCTACAAC GCTTCCAACA A            41

(2) INFORMATION FOR SEQ ID NO: 66:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 66:

AANACCCTGA GCTCATGCCT YTGACCCATG TTCTTGCCAC C            41

(2) INFORMATION FOR SEQ ID NO: 67:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 67:

TTTGGGACCG TTGGAGTTGC RTCTGCGGCT ATGACGGTGG A 41

(2) INFORMATION FOR SEQ ID NO: 68:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 68:

AATCTTTGCC ATTGCTGTCA RTATCTTCGT CAGCTTCAGC T 41

(2) INFORMATION FOR SEQ ID NO: 69:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 69:

GACAACGCTG GTGGTATTGC YGAAATGGCT GGAATGAGCC A 41

(2) INFORMATION FOR SEQ ID NO: 70:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 70:

GCTGCTCTAG GGATGCTCAG YACCATCGCC ACCGGTTTGG C 41

(2) INFORMATION FOR SEQ ID NO: 71:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 71:

ATGCTCAGCA CCATCGCCAC YGGTTTGGCG ATTGATGCTT A 41

(2) INFORMATION FOR SEQ ID NO: 72:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 72:

GAGAAAGTGC TTGTGGAGAT YTACAAGTCC ATACTGATGG C 41

(2) INFORMATION FOR SEQ ID NO: 73:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 73:

AATGCTTGTG GAGATTTACA RGTCCATACT GATGGCGCAG G 41

(2) INFORMATION FOR SEQ ID NO: 74:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 74:

AATGCTTGTG GAGATCTACA RGTCCATACT GATGGCGCAG G          41

(2) INFORMATION FOR SEQ ID NO: 75:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 75:

AATGATTGGT TTGAGAAGCA WACAGCTGGT ACGCTTGATA T          41

(2) INFORMATION FOR SEQ ID NO: 76:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 76:

GATAGGGCGA AGAGAGGGAA RAGTCCTGAG AGGAAAGAGA T          41

(2) INFORMATION FOR SEQ ID NO: 77:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 77:

CTCTCTCTCC ACAAAGACAC MGCTTTCTCC ATGACCTTCG G          41

(2) INFORMATION FOR SEQ ID NO: 78:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 78:

TCTCTGACGT CATGAAAGCT MATGGCAAAA TTGCTGATGG A          41

(2) INFORMATION FOR SEQ ID NO: 79:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 79:

GTTATCGATC GCGTGGTCCG YGAAACCCAA AATACACCTT T          41

(2) INFORMATION FOR SEQ ID NO: 80:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 80:

GTTATCGATC GCGTGGTCCG YGAAACCCAA AATTCACCTT T                          41

(2) INFORMATION FOR SEQ ID NO: 81:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 81:

CGTCAGCCTT CTTCCGCCGC MGTCGTCCTC CGCAACCGTG C                          41

(2) INFORMATION FOR SEQ ID NO: 82:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 82:

TGTCTCTTCC GTCAGCCTTC YTCCGCCGCA GTCGTCCTCC G                          41

(2) INFORMATION FOR SEQ ID NO: 83:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 83:

TGTCTCTTCC GTCAGCCTTC YTCCGCCGCC GTCGTCCTCC G                          41

(2) INFORMATION FOR SEQ ID NO: 84:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ix) FEATURE:
        (A) NAME/KEY: variation
        (B) LOCATION: replace(21, "")
        (D) OTHER INFORMATION: /note= "deletion polymorphism"

(xi) SEQUENCE DESCRIPTION: SEQ ID NO: 84:

TCAGGTTTAC CTCTATATAT TATATTTCAT GGTATGAAGG T                          41

(2) INFORMATION FOR SEQ ID NO: 85:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 85:

TATCCTGCAA ATTGACATTT YCCTTCAGGT TCTAGAAGCT G					41

(2) INFORMATION FOR SEQ ID NO: 86:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ix) FEATURE:
        (A) NAME/KEY: variation
        (B) LOCATION: replace(21, "")
        (D) OTHER INFORMATION: /note= "deletion polymorphism"

(xi) SEQUENCE DESCRIPTION: SEQ ID NO: 86:

CGAGAACAGA AGAGAAGAGA CTGGAACACG TCGGACAGTA C					41

(2) INFORMATION FOR SEQ ID NO: 87:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 87:

ACGGGTCCTA GCGCCATGGC TATTTTCCTC ACCGTTTCTG G					41

(2) INFORMATION FOR SEQ ID NO: 88:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 88:

TTGGGCTTTC GGTGGTATGA TCTTCGTCCT CGTCTATTGC A					41

(2) INFORMATION FOR SEQ ID NO: 89:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 89:

TCCTTGATTC CTTAATAATC WTTGGCTGGG GGTCTTTCTA A					41

(2) INFORMATION FOR SEQ ID NO: 90:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 90:

GCTTGAATAA CGATGTCTAC TCTGCCTCGG CGTACGGCGG A					41

(2) INFORMATION FOR SEQ ID NO: 91:

(i) SEQUENCE CHARACTERISTICS:
        (A) LENGTH: 41 base pairs (B) TYPE: nucleic acid
        (C) STRANDEDNESS: single
        (D) TOPOLOGY: linear (xi) SEQUENCE DESCRIPTION: SEQ ID NO: 91:

CTAAAAAGAT CGACGAGTGT CCCTTACTAC GCTCCATCTA T                         41

(2) INFORMATION FOR SEQ ID NO: 92:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 92:

AGGTGGGTTT AGCGTGGCAT CCGATCCATT GGATGGATCC A                         41

(2) INFORMATION FOR SEQ ID NO: 93:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 93:

NGTGGGTTTA CCGTATCATT TGATCCATTG GATGGATCGA G                         41

(2) INFORMATION FOR SEQ ID NO: 94:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 94:

GCGGATCCTA TATTGGGTCT TGATGGATTG TTTCTATCCC G                         41

(2) INFORMATION FOR SEQ ID NO: 95:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 95:

TATCCTGCAA ATTGACATTT CCCTTCAGGT TCTAGAAGCT G                         41

(2) INFORMATION FOR SEQ ID NO: 96:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 96:

TACCACGGTC GTACTGGTCG ATGTCTGGAA CGTCACCAAG C                         41

(2) INFORMATION FOR SEQ ID NO: 97:

(i) SEQUENCE CHARACTERISTICS:
        (A) LENGTH: 41 base pairs
        (B) TYPE: nucleic acid (C) STRANDEDNESS: single
        (D) TOPOLOGY: linear (xi) SEQUENCE DESCRIPTION: SEQ ID NO: 97:

CTGTCTCAGT TGTTGGATCS AAATCGAAT CGAAAGCGTA C                           41

(2) INFORMATION FOR SEQ ID NO: 98:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 98:

CTGTCTCAGT TGTTGGATCS AAATCAAAT CGAAAGCGTA C                           41

(2) INFORMATION FOR SEQ ID NO: 99:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 99:

ACACTGTTGG AGGACGTGAA GAAGATATTC AAGACAACAT C                          41

(2) INFORMATION FOR SEQ ID NO: 100:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 100:

TCTTTCGTAT CTTGCTGAGT YGTTACGCCT GTCAACACCC G                          41

(2) INFORMATION FOR SEQ ID NO: 101:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 101:

GGAACCCTAG GGAGCCCACA GCTCCTTATG CTAAGCGGCG T                          41

(2) INFORMATION FOR SEQ ID NO: 102:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 102:

GATCATAGTA TCCGCCGGAA CCCTAGGGAG CCCACAGCTC C                          41

(2) INFORMATION FOR SEQ ID NO: 103:

(i) SEQUENCE CHARACTERISTICS:
        (A) LENGTH: 41 base pairs
        (B) TYPE: nucleic acid
        (C) STRANDEDNESS: single (D) TOPOLOGY: linear (xi) SEQUENCE DESCRIPTION: SEQ ID NO: 103:

TTCGGCGGGT CGATCCGGGC RGAAGACATT GTCAGGTGAN N           41

(2) INFORMATION FOR SEQ ID NO: 104:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 104:

GCACCAACAT TGTAAACCTA KAGCTTCTTC CTCAGCCACC T           41

(2) INFORMATION FOR SEQ ID NO: 105:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 105:

GCTGCCACAT AGTGAACCTA WAGCTTCTTC CTCAGCCACC T           41

(2) INFORMATION FOR SEQ ID NO: 106:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 106:

GCACCAACAT TGTGAACCTA RAGCTTCTTC CTCAGCCACC T           41

(2) INFORMATION FOR SEQ ID NO: 107:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 107:

AGTACATAGC TATTGACTAA STTAAGTTCC TTGTATTGTT G           41

(2) INFORMATION FOR SEQ ID NO: 108:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 108:

CCTCTATCCG CCATGGTTGC WCCAACATTG TGAACCTAGA G           41

(2) INFORMATION FOR SEQ ID NO: 109:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 109:

TTGACCCTCG GCAAGCCACC KGTCAAGCCA TGCTGCAGCC T                41

(2) INFORMATION FOR SEQ ID NO: 110:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 110:

AGGCTGCCCT CTCCCAATTC MAAAGCCAAC TCCTAAACCA A                41

(2) INFORMATION FOR SEQ ID NO: 111:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ix) FEATURE:
        (A) NAME/KEY: variation
        (B) LOCATION: replace(21, "")
        (D) OTHER INFORMATION: /note= "deletion polymorphism"

(xi) SEQUENCE DESCRIPTION: SEQ ID NO: 111:

AAACATGGAA AGGCCTGATA GTCACCGTCA AGCTCACCGT C                41

(2) INFORMATION FOR SEQ ID NO: 112:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 112:

CAACCTGAAA AATTGTTTTA MCAACGGCCC CGCTTTCTCC A                41

(2) INFORMATION FOR SEQ ID NO: 113:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 113:

AAGGCCAACA ACGACATTAC CTCCATCGTT AGCAACGGAG G                41

(2) INFORMATION FOR SEQ ID NO: 114:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 114:

TCACCGGCTT GAAGTCTTCC KCTGCATTCC CAGTCACCCG C                41

(2) INFORMATION FOR SEQ ID NO: 115:

(i) SEQUENCE CHARACTERISTICS:

(A) LENGTH: 41 base pairs
        (B) TYPE: nucleic acid
        (C) STRANDEDNESS: single
        (D) TOPOLOGY: linear (ix) FEATURE:
        (A) NAME/KEY: variation
        (B) LOCATION: replace(21, "")
        (D) OTHER INFORMATION: /note= "deletion polymorphism"

(xi) SEQUENCE DESCRIPTION: SEQ ID NO: 115:

ACTCAGCTTT CTTATGCCTC GACTTGCGAC ACACGAATCC A        41

(2) INFORMATION FOR SEQ ID NO: 116:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 116:

TGCGGCTAAC ATCTCTGGTG KTCACCTTAA CCCAGCCGTA N        41

(2) INFORMATION FOR SEQ ID NO: 117:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 117:

CGAGGATCAC TTCTCTCTGT KCAAGAAGAA GTTCGGCAAG G        41

(2) INFORMATION FOR SEQ ID NO: 118:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 118:

CTGTTCAAGA AGAAGTTCGG YAAGGTCTAC GCTTCCCGCG A        41

(2) INFORMATION FOR SEQ ID NO: 119:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 119:

CCCTCTGCTC GTCACGGCGT WACGCAGTTC TCGGATCTGA C        41

(2) INFORMATION FOR SEQ ID NO: 120:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 120:

CCCGCGAGGA GCACGACTAC WGATTCTCCG TTTTCAAATC C        41

(2) INFORMATION FOR SEQ ID NO: 121:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 121:

TCCACTCGCC GGGAAGAAAC TCGACAAACC GTTGTCTACT T           41

(2) INFORMATION FOR SEQ ID NO: 122:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 122:

ATGGCTCGCG ACGGGTCTCC GGTAAACCTC GGAGAGCAGA T           41

(2) INFORMATION FOR SEQ ID NO: 123:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ix) FEATURE:
        (A) NAME/KEY: variation
        (B) LOCATION: replace(21, "")
        (D) OTHER INFORMATION: /note= "deletion polymorphism"

(xi) SEQUENCE DESCRIPTION: SEQ ID NO: 123:

GCCGACTCTC GAAGCTTCTT AACTCCACTC GCCGGGAAGA A           41

(2) INFORMATION FOR SEQ ID NO: 124:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 124:

GAATCTAGGA GAGCAGATCT KCCTCTCTAT CTTCAATGTT C           41

(2) INFORMATION FOR SEQ ID NO: 125:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 125:

TCCACTCGCC GGGAAGAAAC YCGACAAACC GTTGTCTACA T           41

(2) INFORMATION FOR SEQ ID NO: 126:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 126:

GTCATGAAGA TATTCACTAC RCCGACTCTC GAAGCTTCTT A                       41

(2) INFORMATION FOR SEQ ID NO: 127:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 127:

GCAGGTAAAA TTCTACAGAC MTTCCCTTTT CATTGTAGTT A                       41

(2) INFORMATION FOR SEQ ID NO: 128:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 128:

TCTCCTCCGC CGCGCAAGAA RAAATCGACA GCGGCGCGTC T                       41

(2) INFORMATION FOR SEQ ID NO: 129:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 129:

GTGCCCTAAA GATACCCTCA RGCTTGGTGT CTGCGCTAAT G                       41

(2) INFORMATION FOR SEQ ID NO: 130:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 130:

TTCTTCCCAC AGGTGAAACT TGCTAACTTC CTTCCAAAGT A                       41

(2) INFORMATION FOR SEQ ID NO: 131:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (xi) SEQUENCE DESCRIPTION: SEQ ID NO: 131:

TATGTATCAG ACAATGTGT KWGTGACTGT GGTTGCATCC AT                      42

(2) INFORMATION FOR SEQ ID NO: 132:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 132:

GCTAAGCTAC GCAACTGCCA YCAATCAGGG CAAGCTAAAG G                41

(2) INFORMATION FOR SEQ ID NO: 133:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 133:

TATACACTCT TTAAAAGCGT STGTGTGTAC CCATCTCTCT T                41

(2) INFORMATION FOR SEQ ID NO: 134:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 134:

ATGGCTGCGT ATTGGCTGTC YAAGGCTGGA TCTTGGTCCC A                41

(2) INFORMATION FOR SEQ ID NO: 135:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 135:

GGATCCATCT CAACTATGGT MGTATTATCG TTGAGGCTAG G                41

(2) INFORMATION FOR SEQ ID NO: 136:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ix) FEATURE:
        (A) NAME/KEY: variation
        (B) LOCATION: replace(21, "")
        (D) OTHER INFORMATION: /note= "deletion polymorphism"

(xi) SEQUENCE DESCRIPTION: SEQ ID NO: 136:

GTATGTGATT CGGAAGAGAA TCAAACTAAG TGCCGAGAAA G                41

(2) INFORMATION FOR SEQ ID NO: 137:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (xi) SEQUENCE DESCRIPTION: SEQ ID NO: 137:

GCTAAGGTAG TTGGAGGAGC SWRCCACAGC CACGCGACTA AGG              43

(2) INFORMATION FOR SEQ ID NO: 138:

(i) SEQUENCE CHARACTERISTICS:
        (A) LENGTH: 41 base pairs
        (B) TYPE: nucleic acid (C) STRANDEDNESS: single
        (D) TOPOLOGY: linear (xi) SEQUENCE DESCRIPTION: SEQ ID NO: 138:

CTCAACGTAG CAAGTAATAA KATACTGTCT ATTTATGGTT A                    41

(2) INFORMATION FOR SEQ ID NO: 139:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 139:

AGACTTTCCC CATTCTCTTC WCCATCCACC GTCGAAACCC A                    41

(2) INFORMATION FOR SEQ ID NO: 140:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 140:

ACTTCGAAAC TGTAAACCTA WACTTTAAGA GTTTAGAGCT A                    41

(2) INFORMATION FOR SEQ ID NO: 141:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 141:

CACCATCGGA GAAAGAGGTA YTTCGAAACT GTAAACCTAA A                    41

(2) INFORMATION FOR SEQ ID NO: 142:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 142:

CTAAGGCGTC TCCTGAAGAA RTACAGAGAG TCGAAGAAGA T                    41

(2) INFORMATION FOR SEQ ID NO: 143:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 143:

CCGCGGACGA CGCTTTCTTC MTCTGCTCCA CCGCGAGCGC C                    41

(2) INFORMATION FOR SEQ ID NO: 144:

(i) SEQUENCE CHARACTERISTICS:
        (A) LENGTH: 42 base pairs
        (B) TYPE: nucleic acid
        (C) STRANDEDNESS: single (D) TOPOLOGY: linear (ix) FEATURE:
        (A) NAME/KEY: variation
        (B) LOCATION: replace(21, "")
        (D) OTHER INFORMATION: /note= "deletion polymorphism"

(xi) SEQUENCE DESCRIPTION: SEQ ID NO: 144:

GAGGAGTAGT CTCCATGGCC GAAGAAGAGC GTCGGAGACC TG            42

(2) INFORMATION FOR SEQ ID NO: 145:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 145:

GAAGTTAGGG CTTCTAAGAT YAAGTTCGGC AAGGCTTTAA C             41

(2) INFORMATION FOR SEQ ID NO: 146:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 146:

TCAAAACTAA TATTTCTTTT STTGATTGGT AATAAACAGG T             41

(2) INFORMATION FOR SEQ ID NO: 147:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 147:

TTCCAGTGAA AAGGCATTGT KCTCCAAAAT CTCGCTCTGC G             41

(2) INFORMATION FOR SEQ ID NO: 148:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 148:

AAGCAGCTCT GACTTGAATG MGAGAGGTTA ATCAGACTGT G             41

(2) INFORMATION FOR SEQ ID NO: 149:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 149:

TAGATTGAAG CAATCAAGAA RATCTCAGAC TTCATCACCC A             41

(2) INFORMATION FOR SEQ ID NO: 150:

```
    (i) SEQUENCE CHARACTERISTICS:
        (A) LENGTH: 42 base pairs
        (B) TYPE: nucleic acid
        (C) STRANDEDNESS: single
        (D) TOPOLOGY: linear (ix) FEATURE:
        (A) NAME/KEY: variation
        (B) LOCATION: replace(21, "")
        (D) OTHER INFORMATION: /note= "deletion polymorphism"

(xi) SEQUENCE DESCRIPTION: SEQ ID NO: 150:

GCATCCAACT CCAAGGATGA CCCTGCCAAG GTGCTGCTAA CT                              42

(2) INFORMATION FOR SEQ ID NO: 151:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 151:

GAGCTCAGGG ATGGTGGATC WGACTACCTT GGAAAGGGTG T                               41

(2) INFORMATION FOR SEQ ID NO: 152:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 152:

TGGGGTTAGT CGAAATAGGT WAAATGCTTT GAGTATGTGT A                               41

(2) INFORMATION FOR SEQ ID NO: 153:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 153:

TACGCGCAGC ACGGACTTGC RACGCAAGCA ATCGAGCTTT T                               41

(2) INFORMATION FOR SEQ ID NO: 154:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 154:

GAAGCCCATG GTACGGAGCG RGAGAGAGTC AAGTACTTGG G                               41

(2) INFORMATION FOR SEQ ID NO: 155:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 155:

AACGGGTCAC TGCTAAATCA WAAGGATCAC AAGGCTGGGA C                               41
```

(2) INFORMATION FOR SEQ ID NO: 156:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ix) FEATURE:
        (A) NAME/KEY: variation
        (B) LOCATION: replace(21, "")
        (D) OTHER INFORMATION: /note= "deletion polymorphism"

(xi) SEQUENCE DESCRIPTION: SEQ ID NO: 156:

CTAGCCTACT TTGGGAAAAG TTTCGTTATT GTTTTGTGTG G          41

(2) INFORMATION FOR SEQ ID NO: 157:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 157:

GACTTCAAGG ACTTCGCCGG MAAATGCTCC GACGCTGTCA A          41

(2) INFORMATION FOR SEQ ID NO: 158:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 158:

GAGGAGGGCT ACATGCAGCT RAAGAGGCTG AGGGGGCTAA A          41

(2) INFORMATION FOR SEQ ID NO: 159:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 159:

GATGTTCAAC CTATGAAGAA SAAACACCGA GGACCAACGA G          41

(2) INFORMATION FOR SEQ ID NO: 160:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 160:

CCATTAGTGA GGGAGCATGT WCCTGTCACA TTTGATGATT G          41

(2) INFORMATION FOR SEQ ID NO: 161:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (xi) SEQUENCE DESCRIPTION: SEQ ID NO: 161:

AAACACATCG CCAAAGATCC MRACACTCGA GAAAGAGTGG AG                42

(2) INFORMATION FOR SEQ ID NO: 162:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 162:

CTCATAGGCG ATCTGGAGTA KGCAAATCGA ATCTCCTCTC C                 41

(2) INFORMATION FOR SEQ ID NO: 163:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 163:

TGCACGCCTC ACTTGTTCCT WCCAATCTGA CATCAAGGAT T                 41

(2) INFORMATION FOR SEQ ID NO: 164:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 164:

NGTGTTTTTG AGGTGAAAGC WACAAATGGA GATACCTTTT T                 41

(2) INFORMATION FOR SEQ ID NO: 165:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 165:

CCCGAGCCAT TAGGACAAGA YGACTTGCCG TTTGACCAAA C                 41

(2) INFORMATION FOR SEQ ID NO: 166:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 166:

CCCATCTCAT CCTTTCTTGA RCCGTTGAAT CAAGCTCCTG G                 41

(2) INFORMATION FOR SEQ ID NO: 167:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 167:

TACATTCTCA TTGGTTGGTT MTTGGGAAAT AAAGTACCAA C                                41

(2) INFORMATION FOR SEQ ID NO: 168:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 168:

GCACGCGCTA GAGTTGTTGC CAGAAGGAAT GAACAATCTG A                                41

(2) INFORMATION FOR SEQ ID NO: 169:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 169:

CTTGAGACCT ATAGTCCTGT WGTTCGGTCC GCCACAGTTC G                                41

(2) INFORMATION FOR SEQ ID NO: 170:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 170:

CACAGTTCGT ACAGTTCTTC MCATTGCCAC TGTTATGCAC T                                41

(2) INFORMATION FOR SEQ ID NO: 171:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 171:

GAAGGCGTCC ACTATCTTGA RACCTATAGT CCTGTTGTTC G                                41

(2) INFORMATION FOR SEQ ID NO: 172:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 172:

TCCCGGAAAT CTTGCTGAAA MCGTTTACCT GCGACAACCA G                                41

(2) INFORMATION FOR SEQ ID NO: 173:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 173:

ATGTCTTCAA AGTGCTCTGT TGCAACGCAC GTCCGAACAA G        41